US012350310B2

(12) United States Patent
Peel et al.

(10) Patent No.: US 12,350,310 B2
(45) Date of Patent: Jul. 8, 2025

(54) TREATMENT AND PREVENTION OF NEPHROTOXIN-INDUCED KIDNEY INJURIES

(71) Applicant: Farsight Medical Technology (Shanghai) Co., Ltd., Shanghai (CN)

(72) Inventors: Michael Robert Peel, Shanghai (CN); Fashu Ma, Shanghai (CN); Hans Georg Fliri, Shanghai (CN); Ching Pong Mak, Shanghai (CN); Dong Xiao, Shanghai (CN)

(73) Assignee: Farsight Medical Technology (Shanghai) Co., Ltd., Shanghai (CN)

( * ) Notice: Subject to any disclaimer, the term of this patent is extended or adjusted under 35 U.S.C. 154(b) by 550 days.

(21) Appl. No.: 17/767,508

(22) PCT Filed: Oct. 12, 2020

(86) PCT No.: PCT/CN2020/120290
§ 371 (c)(1),
(2) Date: Apr. 8, 2022

(87) PCT Pub. No.: WO2021/068957
PCT Pub. Date: Apr. 15, 2021

(65) Prior Publication Data
US 2023/0173017 A1 Jun. 8, 2023

(30) Foreign Application Priority Data

Oct. 12, 2019  (WO) ................ PCT/CN2019/110777
Sep. 15, 2020  (WO) ................ PCT/CN2020/115299

(51) Int. Cl.
A61K 38/12 (2006.01)
A61P 13/12 (2006.01)

(52) U.S. Cl.
CPC ............. A61K 38/12 (2013.01); A61P 13/12 (2018.01)

(58) Field of Classification Search
None
See application file for complete search history.

(56) References Cited

U.S. PATENT DOCUMENTS

| 6,583,265 | B1 | 6/2003 | Ellmerer-Mueller et al. |
| 8,188,052 | B2 | 5/2012 | Houck |
| 2013/0303438 | A1 | 11/2013 | Su et al. |
| 2017/0035718 | A1 | 2/2017 | Tejedor Jorge et al. |

FOREIGN PATENT DOCUMENTS

| CN | 1176826 A | 3/1998 |
| CN | 1305493 A | 7/2001 |
| CN | 101068829 A | 11/2007 |
| CN | 101437501 A | 5/2009 |
| CN | 101511357 A | 8/2009 |
| CN | 103857407 A | 6/2014 |
| CN | 104603146 A | 5/2015 |
| CN | 105917229 A | 8/2016 |
| CN | 106902346 A | 6/2017 |
| CN | 106902347 A | 6/2017 |
| CN | 111132688 A | 5/2020 |
| CN | 111449050 A | 7/2020 |
| EP | 0194972 A2 | 9/1986 |
| EP | 0484281 A2 | 5/1992 |
| EP | 2742948 A1 | 6/2014 |
| TW | 201639873 A | 11/2016 |
| WO | 9965933 A1 | 12/1999 |
| WO | 2006039668 A2 | 4/2006 |
| WO | 2007136759 A2 | 11/2007 |
| WO | 2008143996 A1 | 11/2008 |
| WO | 2010076329 A1 | 7/2010 |
| WO | 2014049540 A2 | 4/2014 |
| WO | 2014053834 A1 | 4/2014 |
| WO | 2015084939 A1 | 6/2015 |
| WO | 2019016572 A1 | 1/2019 |
| WO | 2021068957 A1 | 4/2021 |
| WO | 2021190601 A1 | 9/2021 |
| WO | 2021190603 A1 | 9/2021 |

OTHER PUBLICATIONS

Naughton "Drug-Induced Nephrotoxicity," American Family Physician (2008) vol. 78, No. 6, pp. 743-750) (Year: 2008).*
Written Opinion of the International Application No. PCT/CN2020/070852, Apr. 3, 2020, 8 pages.
Written Opinion of the International Application No. PCT/CN2020/120290, Jan. 14, 2021, 7 pages.
Written Opinion of the International Application No. PCT/CN2019/110777, Jun. 30, 2020, 6 pages.
Hou, Weiping, et al., "Cyclophilin D promotes tubular cell damage and the development of interstitial fibrosis in the obstructed kidney", Clinical and Experimental Pharmacology and Physiology, vol. 45, 2018, pp. 250-260.
Janowski, B., et al., "A Protease-Free Assay for Peptidyl Prolyl cis/trans Isomerases Using Standard Peptide Substrates", Analytical Biochemistry, vol. 252, 1997, pp. 299-307.
Khalid, Usman, et al., "Kidney ischaemia reperfusion injury in the rat: the EGTI scoring system as a valid and reliable tool for histological assessment", Journal of Histology & Histopathology, vol. 3, Article 1, 2016, pp. 1-7.
Moscoso-Solorzano, Grace, et al., "Cyclophilin A as a mediator of tissue injure and nephrotoxicity", Nephrology Reviews, vol. 4:e9, 2012, pp. 42-44.
Quesniaux, Valerie F. J, et al., "Cyclophilin binds to the region of cyclosporine involved in its immunosuppressive activity", Eur. J. Immunol. vol. 17, 1987, pp. 1359-1365.
Singh, D., et al., "Cyclosporine Protects Against Ischemia/Reperfusion Injury in Rat Kidneys", Toxicology, vol. 207, No. 3, Dec. 22, 2004, pp. 339-347.

(Continued)

Primary Examiner — Christina Bradley
(74) Attorney, Agent, or Firm — Synergy IP Group AG; Lily Ackerman

(57) ABSTRACT

Provided herein is Compound I or a pharmaceutically acceptable salt thereof for use in the prevention and/or treatment of a kidney condition or disease in a subject exposed to a nephrotoxin capable of inducing said kidney condition or disease.

22 Claims, 5 Drawing Sheets

(56) References Cited

OTHER PUBLICATIONS

Tang, Jian, et al., "Using Calcineurin Inhibitor in donor preconditioning reduce ischemia-reperfusion injury in rat renal transplantation and the mechanisms", China Medical Herald, vol. 9, Issue 25, Sep. 2012, pp. 8-10.

Ying, Yuan, et al., "Regulation of necrotic cell death p53, PARP1 and Cyclophilin D—overlapping pathways of regulated necrosis?", Cell Mol. Life Sci., vol. 73 (11-12), 2016, pp. 2309-2324.

Zhou, Jiangqiao, et al., "Protective effect of cyclosporine A on ischemia-reperfusion injury in transplanted kidney", Chinese Journal of Organ Transplantation, vol. 26, No. 6, Jun. 30, 2005, pp. 378-379.

Written Opinion of the International Application PCT/CN2020/084820, Jan. 22, 2021, 13 pages.

Written Opinion of International Application No. PCT/CN2021/087501, Jul. 19, 2021, 9 pages.

"Natural Immunity Applied Giken Increases Sales of LPS", Health Industry Bulletin, Apr. 17, 2018, 2 pages.

An, Jin, et al., "Polydeoxyribonucleotide Ameliorates Lipopolysaccharide-Induced Lung Injury by Inhibiting Apoptotic Cell Death in Rats", International Journal of Molecular Sciences, No. 18, vol. 1847,, Aug. 21, 2017, pp. 1-14.

Fonai, Fruzsina, et al., "Lack of cyclophilin D protects against the development of acute lung injury in endotoxemia", Biochimica et Biophysica Acta 1852, Sep. 15, 2015, pp. 2563-2573.

Hu, Jun-Feng, et al., "The effect of cyclosporine A on lipopolysaccharide-induced acute lung injury in mice", Chinese Journal of Applied Physiology. 31, No. 1, vol. 27, Dec. 31, 2011, pp. 120-123.

Li, Wei-Hua, et al., "Pathophysiology of respiration. Pathology of Respiratory System", Peoples Military Medical Press, Mar. 31, 2011, p. 24.

Liu, Yuning, et al., "Clinical Experiences of National-level Famous Old Chinese Medicine Practitioners Series: Clinical Records of Kidney Diseases", China Medical Science Press, vol. 11, Nov. 30, 2016, pp. 1-6.

Meng, Peng. Z., et al., "Protective Effect of Dexmedetomidine on Endotoxin-Induced Acute Lung Injury in Rats", Med Sci Monit, vol. 24, Jul. 14, 2018, pp. 4869-4875.

Naughton, Cynthia A., "Drug-Induced Nephrotoxicity", vol. 78, No. 6, Sep. 15, 2008, pp. 743-750.

Randjelovic, Pavle, et al., "Gentamicin Nephrotoxicity in Animals: Current Knowledge and Future Perspectives", EXCLI Journal, vol. 16, Mar. 24, 2017, pp. 388-399.

Whiting, P. H., et al., Br. J. exp. Path., vol. 64, 1983, pp. 693-701.

Xiao, Zhenghua, et al., "Attenuation of Lipopolysaccharide-Induced Acute Lung Injury by Cyclosporine-A via Suppression of Mitochondrial DNA", Med Sci Monit; vol. 24, Oct. 27, 2018, pp. 7682-7688.

Yanlei, Pang, et al., "Modern Practical Emergency Medicine", Jilin Science and Technology Press, vol. 1/2, Sep. 30, 2016, pp. 247-261.

\* cited by examiner

TREATMENT AND PREVENTION OF NEPHROTOXIN-INDUCED KIDNEY INJURIES

CROSS REFERENCE TO RELATED APPLICATIONS

This application is a U.S. National Stage Application filed under 35 U.S.C. § 371 claiming the benefit of International Application No. PCT/CN2020/120290, filed on Oct. 12, 2020, which claims priority to and the benefit of International Application No. PCT/CN2020/115299, filed on Sep. 15, 2020, and International Application No. PCT/CN2019/110777, filed on Oct. 12, 2019, all of which are incorporated herein by reference in their entireties.

BACKGROUND OF THE INVENTION

Many approved drug substances are known to be nephrotoxic and may induce kidney conditions such as acute kidney injury or acute kidney failure. Consequently, despite their potential therapeutic value, these types of drug substances are often dose-limited, require careful monitoring for signs of nephrotoxicity when administered to patients, or are simply withheld, in particular from patients with existing or a history of renal impairment. Nephrotoxicity may also arise as a result of pathologies such as rhabdomyolysis, resulting in exposure of kidneys, to endogenous toxins derived from cellular damage or breakdown events which are responsible for transport and excretion of metabolic substances and regulation of water balance amongst other functions.

U.S. Pat. No. 6,583,265 discloses Compound I:

This compound is featured in Example 27 in the patent U.S. Pat. No. 6,583,265, which includes many hundreds of named compounds having modifications at various positions around the ring. However no biological testing data or particular uses are described for this compound or related analogues.

Compound I is also disclosed in WO2019/0169572, for use in the treatment or prevention of acute or chronic inflammatory disorders such as acute kidney injury, ischaemia-reperfusion injury, or chronic or acute pancreatitis. WO2019/0169572 does not disclose use of Compound I in the prevention or treatment of a kidney condition or disease in a subject exposed to a nephrotoxin, wherein the nephrotoxin is a nephrotoxic drug substance, or wherein the nephrotoxin is an endogenous endotoxin. WO2019/0169572 describes a model study for acute kidney injury in mice, based on use of LPS (lipopolysaccharide), which is not a nephrotoxic drug substance but a bacterial endotoxin, the exposure to which leads to sepsis-induced kidney injury.

It is thus an object of the present disclosure and invention to provide for a novel treatment and prophylaxis of kidney conditions or diseases associated with, or induced by exposure to nephrotoxins, and for the protection of kidney from nephrotoxic side effects in subjects receiving treatment with nephrotoxic drug substances, in particular drug substances such as aminoglycoside antibiotics, or chemotherapeutic agents. It is also an object of the present invention to provide for a treatment and prophylaxis of kidney conditions or disease associate with or induced by exposure to endogenous nephrotoxins, caused by conditions such as rhabdomyolysis.

Further objects of the invention will be clear on the basis of the following description of the invention, examples and claims.

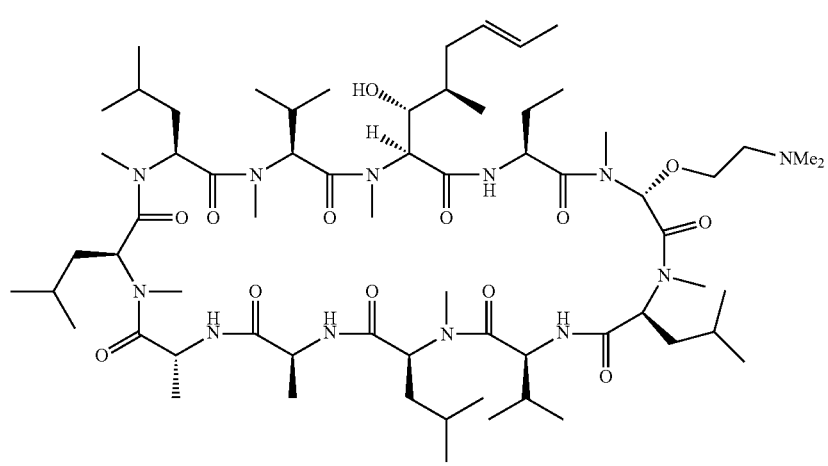

Compound I

SUMMARY OF THE INVENTION

In a first aspect, the present disclosure relates to Compound I or a pharmaceutically acceptable salt thereof

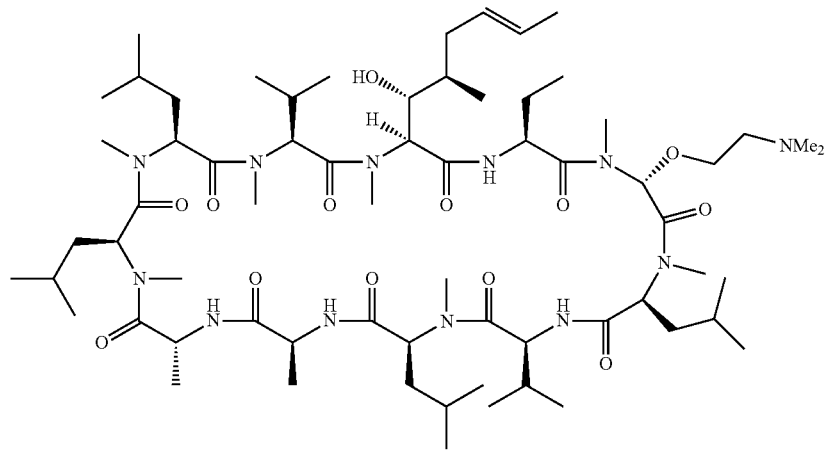

Compound I for use in treating or preventing of a kidney condition or disease in a subject exposed to a nephrotoxin capable of inducing said kidney condition or disease, wherein the nephrotoxin is a nephrotoxic drug substance or an endogenous nephrotoxin. In a further aspect, provided is the use of Compound I or a pharmaceutically acceptable salt thereof in the manufacture of a medicament for the prevention or treatment of a kidney condition or disease in a subject exposed to a nephrotoxin, i.e. a nephrotoxic drug substance or an endogenous nephrotoxin capable of inducing said kidney condition or disease. In yet a further aspect, the current disclosure provides for a method of preventing a kidney condition or disease induced by exposure to a nephrotoxic drug substance or an endogenous nephrotoxin in a subject, the method comprising administering Compound I or a pharmaceutically acceptable salt thereof to said subject. In further aspect, the nephrotoxin is an aminoglycoside.

(Group 2, one dose per day each of vehicle and gentamicin), G3 (Group 3, one dose per day of 0.5 mg/kg Compound I and one dose per day of gentamicin); G4 (Group 4, one dose per day 3 mg/kg Compound I and one dose per day of gentamicin); G5 (Group 5, one dose per day 9 mg/kg of Compound I, and one dose per day of gentamicin). * refers to P<0.05;  refers to P<0.01; * refers to P<0.001 versus G2, based on one-way ANOVA; Dunnett's multiple comparison test.

Figure 5:
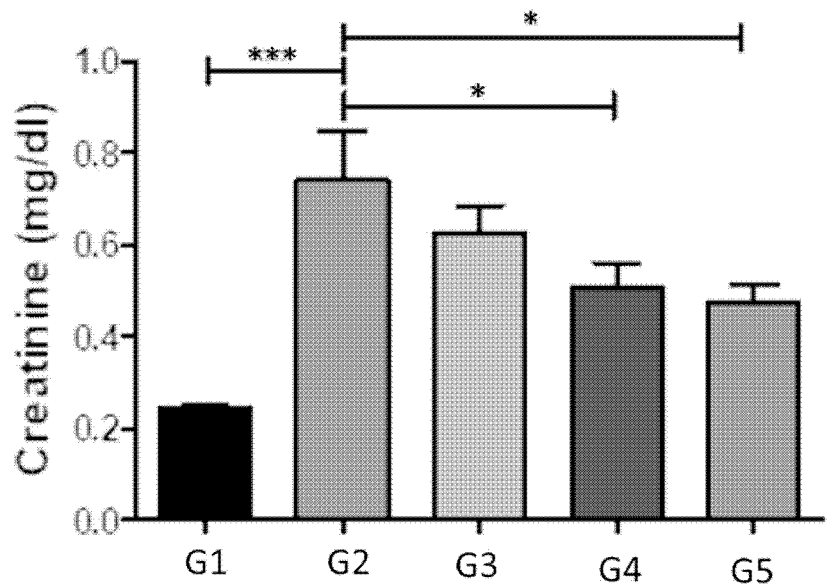
FIG. 5 depicts the study endpoint serum creatinine levels. Depicted from left to right on the x-axis are: G1 (Group 1, control; no treatment with gentamicin or Compound I); G2
Figure 6:
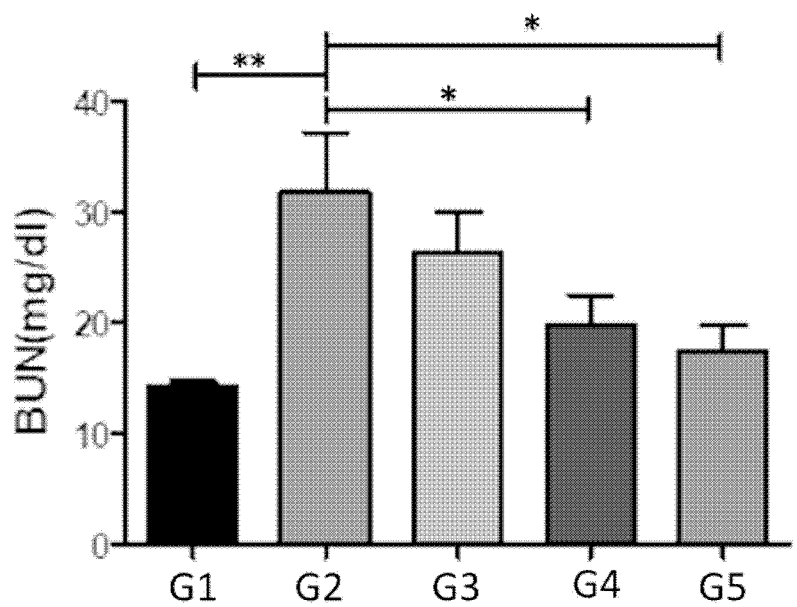

FIG. 6 depicts the study endpoint serum urea nitrogen (BUN) levels. Depicted left to right axis are the serum BUN levels determined for the study groups G1-G5, which are as described in FIG. 5. * refers to P<0.05;  refers to P<0.01; * refers to P<0.001 versus G2, based on one-way ANOVA; Dunnett's multiple comparison test.

Figure 7:
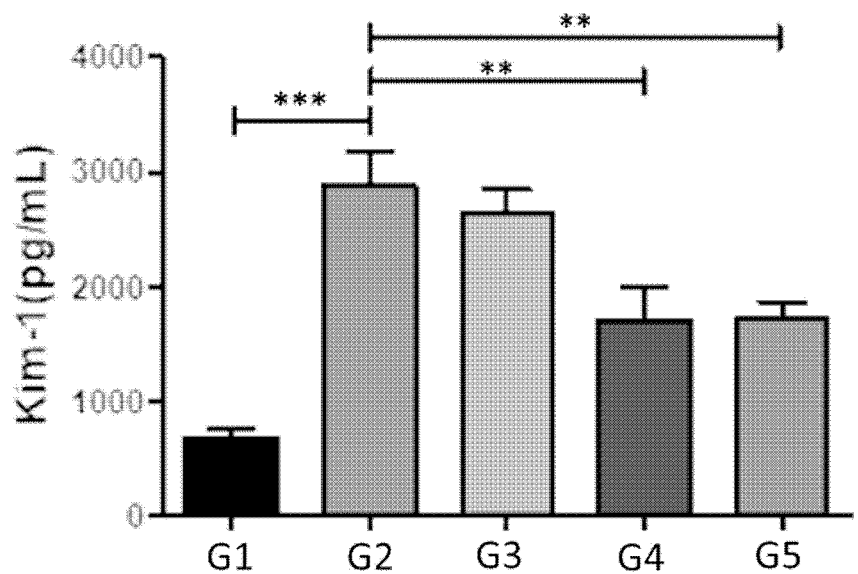

FIG. 7 depicts the study endpoint levels of the acute kidney injury biomarker Kim-1 (kidney injury molecule-1) in plasma. Depicted left to right axis are the measurements obtained for study groups G1-G5 as described in FIG. 5. * refers to P<0.05;  refers to P<0.01; * refers to P<0.001 versus G2, based on one-way ANOVA; Dunnett's multiple comparison test.

Figure 8:
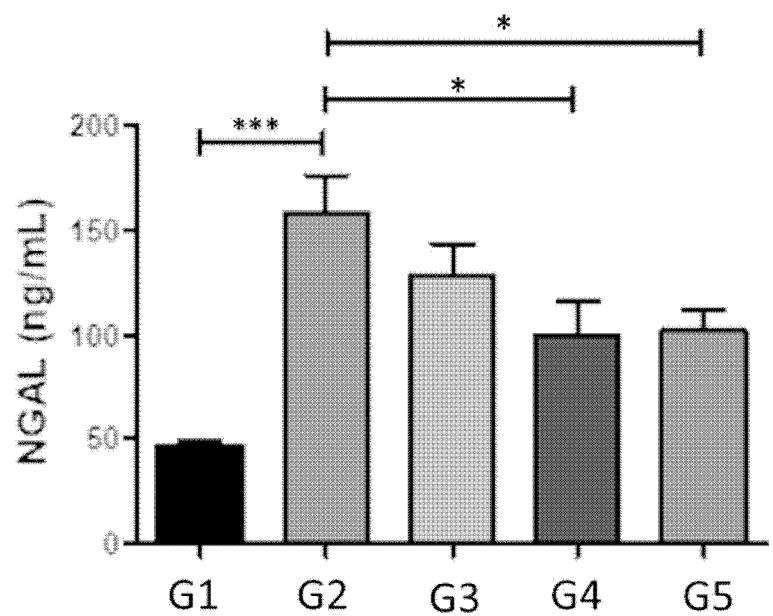

FIG. 8 depicts the study endpoint measurements obtained for the acute kidney injury biomarker NGAL (neutrophil gelatinase-associated lipocalin) in plasma. Depicted left to right axis are the measurements obtained for study groups G1-G5 as described in FIG. 5. * refers to P<0.05;  refers to P<0.01; * refers to P<0.001 versus G2, based on one-way ANOVA; Dunnett's multiple comparison test.

DETAILED DESCRIPTION OF THE INVENTION

In a first aspect, the present disclosure relates to Compound I or a pharmaceutically acceptable salt thereof for use in treating or preventing of a kidney condition or disease in a subject exposed to a nephrotoxin capable of inducing said kidney condition or disease, wherein the nephrotoxin is a nephrotoxic drug substance or an endogenous nephrotoxin.

Compound I is a derivative of cyclosporin A, substituted at position 3 (sarcosine, otherwise known as N-methylglycine) by a N,N-dimethylaminoethoxy residue, and its synthesis and preparation has been described, for example in WO2019/0169572. Compound I as depicted above may be referred to in accordance with one of its chemical names as [(R)-2'-(2-dimethylaminoethoxy)-Sar]$^3$ cyclosporin A. It is to be understood herein that the Compound I as described within the context of the present disclosure and invention, may refer also to in addition to any pharmaceutically acceptable salt thereof, also its enantiomer, diastereomers or racemates as well as its polymorphs, hydrates or complexes. In an alternative and optional embodiment, Compound I may be provided as a mixture of the (R) and (S) stereoisomers at the 3-sarcosine position. Included is also the use of an optically pure stereoisomer of Compound I, as well as the use of a combination of its stereoisomers. The phase 'optically pure', interchangeable with the term 'stereochemically pure' refers to a compound having a level of stereochemical purity as recognized by one skilled in the art, based on conventional methods for the determination of stereochemistry and stereochemical purity. In a further and optional embodiment, Compound I or a pharmaceutically acceptable salt thereof may be provided as an isotope, for example where one or more of its atoms is replaced with a isotope such as $^{13}C$, or with deuterium.

Nephrotoxins are compounds or substances which are capable of disrupting or impairing the function of a subject's kidney(s) and its associated tissues. In one embodiment of the disclosure, the nephrotoxin capable of inducing a kidney condition or disease is a nephrotoxic drug substance.

As used herein, the term 'nephrotoxic drug substance' is an active pharmaceutical ingredient, or a pharmacologically- or diagnostically-active compound or mixture of compounds useful for medical or therapeutic applications in the prevention, diagnosis, stabilization, treatment or management of a condition, disorder or disease and which is capable of disrupting, impairing, or reducing renal function. A nephrotoxic drug substance may be provided or administered to a subject as a medicament or pharmaceutical dosage form comprising said nephrotoxic drug substance or a mixture of nephrotoxic substances, and one or more non-pharmacologically active excipients or carriers. In particular, a nephrotoxic drug substance may be a dose-limited drug substance where administration for its indicated therapeutic or diagnostic applications is restricted in terms of a threshold dose amount given at a single and/or cumulative dose due to its potential for nephrotoxic side effects. A nephrotoxic drug substance may also be further defined as a drug substance for which nephrotoxicity is listed as a side effect or as an adverse effect as per its prescribing information, and/or

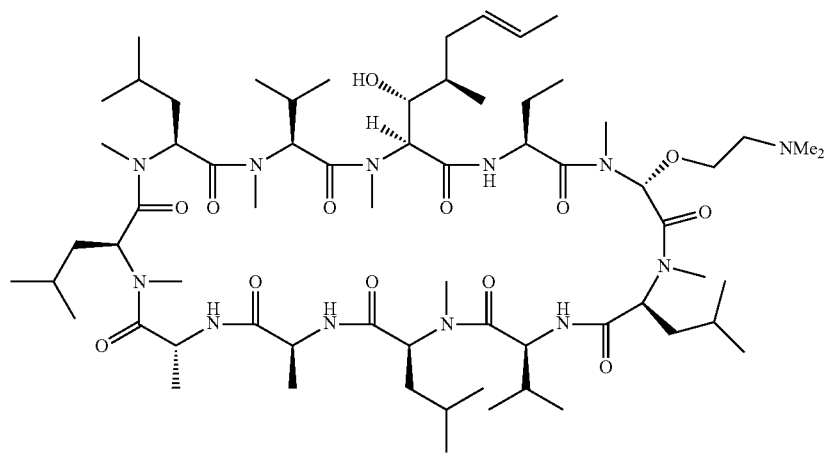

Compound I where its prescribed use for its intended therapeutic/diagnostic application includes an advisory for the monitoring of the dose concentration of the nephrotoxic drug substance (e.g. its serum concentration) in a subject to which it is administered, and/or the renal function of the recipient subject, for example, for signs and markers associated with nephrotoxicity.

As understood herein, the phrase 'exposure to a nephrotoxin' or similar, may refer to the exposure of a subject to a nephrotoxin during the course of a treatment for a condition, symptom or disease, wherein a subject is administered for therapeutic or diagnostic purposes, one or more doses of a nephrotoxin such as any one or combination of the nephrotoxic drug substances as defined in various embodiments herein. The phrase 'exposure to a nephrotoxin' as used herein also comprises any unintended exposure of a subject to a nephrotoxin, for example, but not limited to, accidental exposure such as from a needle-stick injury, or situational/unanticipated circumstances such as physical trauma or prolonged physical stress which may cause the release and/or build-up of endogenous nephrotoxins.

In one embodiment, the nephrotoxic drug substance is selected from the group consisting of antimicrobial agents, cancer chemotherapeutic agents, blood pressure medicines including ACE inhibitors and angiotensin receptor blockers, macrolactone immunosuppressive agent, HIV protease inhibitors, peptic ulcer medicines, non-steroidal anti-inflammatory drugs, proton pump inhibitors, laxatives and contrast agents.

As understood herein, the term 'drug substance', as well as its genus, family, or species may refer to the drug substance as such, as well as any pharmaceutically acceptable salt, hydrate, derivative, or prodrug thereof. For example, the term 'gentamicin' may include also its common commercially available form, gentamicin sulfate. Similarly, the term 'aminoglycosides', interchangeable with the term 'aminoglycoside antibiotics' for example refers to any compound falling within its common definition or classification in the art.

In one particular embodiment, the nephrotoxic drug substance is a chemotherapeutic agent. The chemotherapeutic agent is preferably an cytotoxic or antineoplastic agent used in the treatment cancer in a subject, for example for the targeting and killing of tumour cells. In one specific embodiment, the chemotherapeutic agent is selected from the group consisting of platins (e.g. carboplatin, cisplatin, oxaliplatin or nedaplatin), anthracyclines (e.g. daunorubicin, doxorubicin, idarubicin, epirubicin), bleomycin, mitomycins, actinomycins, cyclophosphamides, capecitabine, cytarabine, gemcitabine, ifosfamide, interleukin-2, streptozocin, gemtuzumab ozogamicin, melphalan, methotrexate, pemetrexed, plicamycin, and trimetrexate.

Preferably, the chemotherapeutic agent is cisplatin. Cisplatin, a platinum complex, is used to treat a variety of cancers including ovarian, lung, head, neck, testicular, and bladder cancers. However, high doses are restricted as cisplatin may induce cumulative and dose-dependent nephrotoxicity. Cisplatin is taken up by renal tubular cells, especially the proximal tubular cells of the inner cortex and outer medulla. These cells and sites are subject to injury and necrotic cell loss, resulting in acute kidney injury and impairment of renal function. Renal toxicity becomes more severe with repeated courses of treatment with cisplatin, and methods for reduction of nephrotoxicity of cisplatin include the use of a 6 to 8 hour infusion with intravenous hydration. In a specific embodiment of the present disclosure, Compound I is used for the treatment and/or prevention of cisplatin-induced acute-kidney injury.

In one embodiment, Compound I or a pharmaceutically acceptable salt thereof is administered to a subject undergoing cancer treatment, wherein the cancer treatment comprises administration of a chemotherapeutic agent to the subject. In one embodiment, the subject may be administered a dose of Compound I prior to receipt of a dose of the chemotherapeutic agent, for example a dose of cisplatin. Compound I may be also administered throughout a treatment course of chemotherapy, or may be administered to a subject undergoing cancer treatment with a chemotherapeutic agent, said subject having developed a kidney condition or disease subsequent to, or as a result of exposure to said chemotherapeutic drug. Said chemotherapeutic drug may be cisplatin.

In another embodiment of the present disclosure, the nephrotoxic drug substance is an antimicrobial agent. Preferably, the antimicrobial agent is an antibiotic agent which is active against bacteria, for example gram-negative and/or gram-positive bacteria).

In one embodiment, the antimicrobial agent may be selected from a group consisting of aminoglycosides, beta-lactams, polypeptide antibiotics, glycopeptide antibiotics peptidomimetic antibiotics, outer membrane protein targeting antibiotics and antifungal agent (e.g. amphotericin B) and combinations thereof.

In one specific embodiment, Compound I or a pharmaceutically acceptable salt thereof is used for the prevention or treatment of a kidney condition or disease induced by exposure to a nephrotoxic drug substance, wherein the drug substance is an aminoglycoside antibiotic. Aminoglycoside antibiotics are used in particular for clinical management and treatment bacterial infections, in particular gram-negative bacterial infections. Aminoglycosides have been found to contribute to renal tubule cells injury and necrosis. Compound I may be used, for the protection of renal function in subjects receiving aminoglycoside antibiotic treatment. In one embodiment, the aminoglycoside antibiotic is selected from the group consisting of gentamicin, tobramycin, amikacin, netilmicin, apramicin, streptomycin, kanamycin, neomycin and sisomycin.

In a preferred embodiment, the aminoglycoside antibiotic is gentamicin. Gentamicin is administered as an injection (intramuscular or intravenously) for the treatment of serious infections caused *Staphylococcus* species, *Citrobacter* species, *Enterobacter* species, *Escherichia coli, Klebsiella-Enterobacter-Serratia* species, *proteus* species and *Pseudomonas aeruginosa*. While effective as an antibiotic, its use requires careful monitoring and control by a clinician, due to its potential for adverse renal effects and nephrotoxicity, which is characterized by rise in renal function markers such as blood urea nitrogen (BUN), serum creatinine, or oliguria. Dosing of gentamicin needs to be carefully monitored, and adjusted and closely monitored, especially for patients with impaired renal function in order to maintain a therapeutically relevant but not excessive levels of the drug.

It has been found by the inventors that Compound I provides a significant protective effect against reduction in kidney function, as demonstrated in a model study based on gentamicin-induced kidney conditions, i.e. acute kidney injury. In one particular embodiment of the present disclosure, Compound I or a pharmaceutically acceptable salt thereof is used for the treatment and/or prevention of gentamicin-induced acuted kidney injury. Compound I may be used for the treatment of a subject suffering from an infection requiring treatment with gentamicin, wherein said subject is administered gentamicin. In one embodiment, a dose of Compound I is administered to a subject prior to administration of a dose of gentamicin. In another embodiment, Compound I is administered to a subject after the onset of reduced renal function, for example subsequent to exposure to gentamicin.

In a further embodiment, the antimicrobial agent is a beta lactam. Examples of beta-lactam antibiotics include but are not limited to cephalosporins, and penicillins, including ureidopenicillins (e.g. piperacillin), aminopenicillins, carboxypenicillins, carbapenems. Also include within the context of the present disclosure, are combination treatments with beta-lactamase inhibitors such as tazobactam, sulbactam, and clavulanic acid.

In another embodiment, the antimicrobial agent is a polypeptide, glycopeptide or peptidomimetic antibiotic. Examples of a polypeptide antibiotics which may comprise of non-ribosomal polypeptides, include bacitracin, and polymyxins such as polymyxin A, B, C, D, E (colistin). Examples of glycopeptide peptides are vancomycin, teicoplanin. The antimicrobial agent may be based on a naturally derived peptide or glycopeptide or alternatively may be a synthetic or semi-synthetic e.g. a peptidomimetic compound, with amino acid modifications. An example of a peptidomimetic antibiotic is murepavadin, an outer membrane protein-targeting antibiotic for use in the treatment of serious infections associated with *Pseudomonas aeruginosa.*

In one embodiment, the antimicrobial agent is murepavadin. In one embodiment, Compound I or a pharmaceutically acceptable salt thereof is administered to a subject suffering from an infection (e.g. a *Pseudomonas aeruginosa* infection), wherein said infection is treated by the administration of murepavadin. In said embodiment, a dose of Compound I may be administered prior to the administration of a dose of murepavadin. Compound I may be administered also throughout the course of prescribed treatment with murepavadin.

In another embodiment, Compound I or a pharmaceutically acceptable salt thereof is administered to a subject suffering from an infection (e.g. a bacterial and/or fungal infection), wherein said infection is treated by administering the antimicrobial agent to the subject. In one embodiment, the subject may be administered a dose of Compound I prior to receipt of a dose of the anti-microbial agent, for example prior to receiving a dose of gentamicin. Compound I may be also administered throughout a treatment course of the antimicrobial agent, or may be administered to a subject undergoing treatment with said antimicrobial agent, who has developed a kidney condition or disease subsequent or as a result of exposure to said antimicrobial agent. In said embodiments, preferably the antimicrobial agent is an aminoglycoside antibiotic such as gentamicin.

In an alternative embodiment, the antimicrobial agent is an anti-fungal agent active against fungal species such as but not limited to *Aspergillus, Candidia, Cryptococcus*, and used for treatment of subjects suffering from fungal infections. Examples of anti-fungal agents include 5-fluorocytosine, amphotericin B, fluconazole, and caspofungin.

In yet another embodiment, the nephrotoxic drug substance is a blood pressure controlling medication or medicine, such as an ACE (angiotensin-converting-enzyme) inhibitor, or an angiotensin receptor blocker. Compound I or a pharmaceutically acceptable salt thereof may be administered to a subject suffering from high blood pressure or a condition requiring reduction of blood pressure, wherein said conditions are treated by administration of said blood pressure controlling medication or agent to the subject.

Examples of ACE inhibitors include, but are not limited to captopril, ramipril, benazepril, enalapril, fosinopril, lisonopril, quinapril. Examples of angiotensin receptor blockers include, but are not limited to candesartan, valsartan, telmisartan, irbesartan, olmesartan, telmisartan, eprosartan, and losartan.

In another embodiment, the nephrotoxic drug substances is a macrolactone immunosuppressive agent. These compounds, which are also referred to as macrolide immunosuppressants, may be used in the prevention or treatment of conditions or diseases such as organ transplant rejection, in an organ transplant recipient. In one embodiment, the macrolactone immunosuppressive agent is tacrolimus, or an mTor inhibitor such as sirolimus (rapamycin).

In another embodiment, the nephrotoxic drug substance is an HIV protease inhibitor. Compound I, or a pharmaceutically acceptable salt thereof may be administered to a subject diagnosed or suffering from HIV or a related condition, wherein said HIV or related condition is treated by administering the HIV protease inhibitor to the subject. Examples of HIV protease inhibitor include, but are not limited to indinavir and ritonavir.

In one embodiment, the nephrotoxic drug substance is a peptic ulcer drug or medication. Compound I or a pharmaceutically acceptable salt thereof may be administered to a subject diagnosed or suffering from a ulcer e.g. a stomach ulcer, wherein ulcer is treated by administering the peptic ulcer drug or medication to the subject. Examples of peptic ulcer drugs include, but are not limited to, cimetidine, esomeprazole, lansoprazole, omeprazole, pantoprazole, and rabeprazole.

In one embodiment, the nephrotoxic drug substances is a non-steroidal anti-inflammatory drug (NSAID). Compound I or a pharmaceutically acceptable salt thereof may be administered to a subject suffering from pain, fever and/or inflammation, wherein said pain, fever and/or inflammation is treated by administering the non-steroidal anti-inflammatory drug (NSAID) to the subject. Alternatively, Compound I may also be administered to a subject having taken an overdose of an NSAID. Examples of NSAIDs, include but are not limited to ibuprofen, ketoprofen, diclofenac and aspirin.

In one embodiment, the nephrotoxic drug substance is a laxative. Compound I or a pharmaceutically acceptable salt thereof may be administered to a subject suffering from constipation, wherein said constipation is treated by administering the laxative to the subject. Alternatively, Compound I may also be administered to a subject having taken an overdose of a laxative. An example of a laxative in the context of the present disclosure is sodium phosphate.

In yet another embodiment, the nephrotoxic drug substance is a contrast agent. A contrast agent is a substance used as a diagnostic tool for the visualization of internal organs or tissues. The contrast agent may be administered intravenously. In one specific embodiment, the contrast agent is an iodinated contrast agent, for example, but not limited to diatrizoate, iothalamate, iohexol, iodixanol, or iopamidol. Compound I or a pharmaceutically acceptable salt thereof may be used in the prevention or treatment of contrast-agent induced acute kidney injury or nephropathy, and may be administered to a subject undergoing, having undergone, or requiring diagnosis using a contrast agent, such as an iodinated contrast agent.

The subject to be treated with or administered with Compound I or a pharmaceutically acceptable salt thereof may, in one embodiment, be administered an nephrotoxic drug as a therapeutic remedy or for an in vivo diagnostic application. In other embodiments, the subject may be receive more than one nephrotoxic drug substance. For example, the subject treated or administered with Compound I may be concomitantly receiving more than one drug substance, for example as a combination treatment, or alternatively, as separate treatment for different conditions or different aspects or symptoms relating to a condition or disease. In one embodiment, the subject to which Compound I is administered may be undergoing a course of treatment with a specific combination of a nephrotoxic drug substance, and a second further drug substance (e.g. piperacillin/tazobactam) optionally wherein the second further drug substance is also a nephrotoxic drug substance. In one embodiment, treatment with one nephrotoxic drug may predispose or enhance the risk of nephrotoxicity of another (nephrotoxic) drug substance. In other embodiments, the subject may be receiving more than one drug substance during a time period in which Compound I is administered.

In another embodiment of the disclosure, the nephrotoxin capable of inducing a kidney condition or disease is an endogenous nephrotoxin. As defined herein, an endogenous nephrotoxin is a molecule or substance (e.g. a protein) produced endogenously by a subject and is not externally administered, in contrast to the nephrotoxic drug substances described above, which may be considered as exogenous toxins. The endogenous nephrotoxin may be present in the subject or a subject's blood or blood serum at a non-nephrotoxic concentration or amount during normal physiological and homeostatic conditions, however at elevated levels i.e. above a threshold or baseline concentration may become nephrotoxic, degrade or breakdown to nephrotoxic components and/or trigger cellular or inflammatory response events leading to onset of nephrotoxicity, and kidney tissue injuries.

In one embodiment, the endogenous nephrotoxin is myoglobin, and optionally any breakdown or degradation products or released components associated with myoglobin. Myoglobin is an oxygen and iron binding protein found in muscle tissue. High levels of myoglobin and its related components may be directly toxic to kidney tubular cells, and may also lead to renal vasoconstriction, formation of intratubular casts amongst other pathologies.

Rhabdomyolysis is a condition characterized by injury or breakdown of skeletal muscle tissue, wherein their contents are released into circulation. The release of high levels of myoglobin is also associated with the related condition of myoglobinuria. Other conditions where endogenous cellular components may become nephrotoxic include, but are not limited to, conditions such as hemolysis (red blood cell lysis, where contents of damaged red blood cells e.g. heme are released into circulation), and also tumour lysis, or myeloma. Tumours in cancer patients may lyse (for example in the course of chemotherapy) and release tumour cellular content into circulation and to the kidneys.

In particular, a subject may suffer from, or may be at risk to suffer from rhabdomyolysis, and its related conditions and be at risk for exposure to endogenous nephrotoxins such as myoglobin due to a number of factors, in particular physical activity or trauma. In one embodiment, Compound I or a pharmaceutically acceptable salt thereof is used for the prevention and/or treatment of a kidney condition or disease induced by exposure to an endogenous nephrotoxin (e.g. rhabdomyolysis or myoglobinuria-induced acute kidney injury), and is administered to a subject having experienced, or is suffering from any one or combination of: physical trauma, crush injury, extreme physical exertion or activities, temperature extremes, exposure to electrical current, and other activities or events which may lead to muscle tissue damage and the breakdown of muscle fibres and/or blood cells.

In a further and related embodiment, Compound I or a pharmaceutically acceptable salt thereof may be administered to the subject prior to exposure to, or engagement with activities (e.g. extreme physical activity or exertion) associated with, or at risk for onset of rhabdomyolysis. Extreme or physical activity or exertion may for example be strenuous exercise which causes or results in skeletal muscle injury as well as optionally severe dehydration.

Subjects which may be at risk for onset of rhabdomyolysis includes subjects exposed to toxins, or drug substances, such as statins which may potentially cause or lead to myopathy. Optionally, Compound I or a pharmaceutically acceptable salt thereof may also be used for the prevention or treatment of rhabdomyolysis and its associated conditions or diseases in a subject with an inherited myopathy.

Compound I or a pharmaceutically acceptable salt thereof is provided, in another embodiment, for use in the prevention and/or treatment of rhabdomyolysis hemolysis, myoglobinuria, or optionally tumour lysis or myeloma-induced acute kidney injury, or failure.

In a related embodiment, the subject to which Compound I or a pharmaceutically acceptable salt thereof may be administered may have elevated serum and/or urine myoglobin levels, i.e. elevated concentration of myoglobin in blood serum and/or in urine. Alternatively, or in addition, said subject may also have any one or combination of elevated serum levels, i.e. elevated serum concentrations of: creatine phosphokinase, lactate dehydrogenase, calcium, potassium, phosphates; indicating the presence of muscle damage. In a further related embodiment, the subject to which Compound I or a pharmaceutically acceptable salt thereof is provided has a serum creatine phosphokinase level of at least 5 times higher than baseline.

As defined herein, the term 'baseline' used in connection with serum concentration levels of creatine phosphokinase refers to a clinically applicable or expected serum creatine phosphokinase level or range for an individual not yet been exposed to a nephrotoxin, or nephrotoxic levels or concentrations of an endogenous nephrotoxin e.g. myoglobin, factoring in variability which may be due to any one or combination of criteria such as, but not limited to, age-group, gender, existing co-morbidities and the like. The baseline value or baseline range for serum creatine phosphokinase, or any of the other markers may be within the knowledge of the skilled clinician or may be determined based on common methods of the art.

As used herein, the term 'treating' or 'treatment' which may be used interchangeably with the term 'therapy' relates to a therapeutic intervention capable of effecting a cure, improvement, amelioration, control, control of progression, prevention of progression of a disease or a condition or symptom associated with said disease or condition.

As understood herein the term 'prevention', which may be used interchangeably with the term 'prophylaxis' refers to the use of a compound, or composition, for preventing the occurrence of a disease, condition or symptom, or significantly reducing the likelihood of occurrence of a disease, condition or symptom, as well as the prevention of, for example, a further reoccurrence of a disease, condition or associated symptom. Also included within the meaning of the term is the prevention of progression of a disease, condition or associated symptom, after an initial improvement or after initial removal of the cause of the disease, condition or symptom.

It may also be understood that any one, or combination of uses, and methods of treatment or prophylaxis as described herein comprises the administration to a subject in need thereof, a pharmacologically effective amount of Compound I. A pharmacologically effective amount refers to an amount, dose, concentration or strength of the compound or compound equivalent which is useful or capable of producing, or contributing to a desired therapeutically and/or prophylactically-relevant pharmacological effect.

In one embodiment, the nephrotoxic drug substance is administered repeatedly to a subject. In other words, the drug substance is administered more than once, i.e. at least twice. The nephrotoxic drug substance may be administered at regular intervals over a period of time, such as over the course of a clinically-determined treatment period. In some embodiments, the nephrotoxic drug substance may be administered administered at least once daily over a period of at least 3 days, or at least 7 days, or may be administered at least once daily between 7 and 10 days. In an alternative embodiment, the nephrotoxic drug substance may be administered once, for example for a diagnostic use.

Compound I or a pharmaceutically acceptable salt thereof may be used for the prevention and/or treatment of a kidney condition or disease in a subject induced by a nephrotoxic drug substance, or an endogenous nephrotoxin. In a preferred embodiment, kidney condition or disease is a nephrotoxin-induced acute kidney injury or kidney failure. In one embodiment, the induced acute kidney injury is a prerenal acute kidney injury, for example associated with a reduced blood flow to the kidneys. For example, ACE inhibitors and angiotensin receptor blockers can impair renal perfusion. NSAIDs may also decrease glomerula filtration rate. In further embodiment, the induced acute kidney injury is intrinsic, with damage to cellular or tissues to the kidney, including to the glomerulus, tubules (acute tubular injury or necrosis), interstitium and/or vasculature. Acute tubular injury or necrosis may occur, for example due to accumulation or localization of a cytotoxic drug substance to the tubular cells.

As understood herein, the term 'subject' may be used interchangeably with the term 'patient'. In one preferred embodiment, the subject is a human subject. In an optional embodiment, the subject may be other animals, such as other mammals. In an optional embodiment, the invention may also have application, for instance, in farm animals or other veterinary subjects, in particular mammals such cats, dogs, primates, horses, cows, and pigs.

In one embodiment, Compound I or a pharmaceutically acceptable salt thereof is administered to a subject having a pre-existing condition or disease, which increases the subject's risk of developing a kidney condition or disease when exposed to a nephrotoxin as defined herein. For example, the subject may have an existing condition or comorbid disease such as existing dysfunction or impairment in an organ such as the lung (e.g. chronic obstructive pulmonary obstruction), liver (e.g. a chronic liver disease) or heart (for example coronary artery disease, or heart failure), and/or may have recently undergone major surgery associated with said organ. In a further embodiment, the subject is geriatric (of advanced age) and/or has diabetes.

In a further embodiment, the subject may also have already existing condition of the kidney, for example chronic kidney disease; polycystic kidney disease, kidney stones, or kidney inflammation. Optionally, the subject has a history of renal impairment, and/or requires dialysis.

In yet a further embodiment, Compound I or a pharmaceutically acceptable salt thereof is administered to a subject with reduced renal function. Reduced renal function may be characterized by any one or combination of: blood urea nitrogen (BUN) levels at least 1.5 to 3 times higher than baseline, and/or serum creatinine levels at least 1.5 to 3 times higher than about baseline, and/or oliguria. In one embodiment, the subject has reduced renal function characterized by serum creatinine and BUN levels at least 2 times higher than baseline.

As defined herein, the term 'baseline' used in connection with serum levels, i.e. serum concentration of creatinine and/or blood urea nitrogen (BUN) levels, i.e. blood urea nitrogen concentration, may refer to the baseline values of these renal function markers which were determined for a subject prior to commencement of exposure to a nephrotoxic drug substance (e.g. prior to a treatment regimen comprising administration of a nephrotoxic drug substance). In circumstances where the subject has not had serum creatinine or BUN levels measured prior to exposure to the nephrotoxin and prior to the onset of reduced renal functions, the term 'baseline' may refer to the clinically applicable or expected serum creatinine and/or blood urea nitrogen values, or range of values for an individual not yet exposed to the nephrotoxin, factoring variability which may be due to criteria such as, and not limited to, age-group, gender, existing co-morbidities and the like. These baseline values or range of values may be within the knowledge of the skilled clinician, and/or may be determined within common methods of the art.

Compound I, or a pharmaceutically acceptable salt thereof may be administered, in one embodiment, to a subject prior the subject's exposure to a nephrotoxic drug substance. Administration of Compound I prior to exposure, as understood herein refers to administration of a first dose of Compound I before a first dose of a nephrotoxic drug is administered.

Additionally, a dose of Compound I, or a pharmaceutically acceptable salt thereof, in some embodiments, may be administered before any dose of the nephrotoxic drug substance is administered, such as if a nephrotoxic drug substances is administered repeatedly e.g. more than once during its prescribed course of treatment. Doses of Compound I may thus be administered in a period between successive doses of the nephrotoxic drug substance. Optionally, more than one dose of Compound I may be administered in a period between successive doses of a nephrotoxic drug substance.

In one embodiment, the present disclosure provides for Compound I or a pharmaceutically acceptable salt thereof for use in the prevention or treatment of a kidney condition or disease induced by a nephrotoxic drug substance (e.g. acute kidney injury) as defined herein, wherein Compound I or a pharmaceutically acceptable salt thereof is administered repeatedly to a subject during a first period of time which commences before and overlaps with a second period of time wherein the subject is exposed to, or is administered repeatedly the nephrotoxic drug substance. As used herein, 'repeatedly' refers to administration or exposure at least twice, i.e. more than once. The period of time may be understood as a course or period of treatment which is clinically determined for example as therapeutically relevant in regards to intended pharmacological effect in prevention, stabilization, treatment or management of the condition, disorder or disease.

As used herein, the term 'dose' or 'dosage' as such refers to a single, or unit dose of Compound I or a pharmaceutically acceptable salt thereof, or a drug substance, unless prefaced or followed by an indication of time, time interval or indication of quantity. A 'daily dose' or 'dosage per day' for example refers to the total dose amount of Compound I or drug substance administered in the course of one day (24 hours). A daily dose may comprise only one dose, if only one dose is administered once per day but may also be a total based on the sum of multiple unit doses that administered during a day, for example, if more than one unit dose is administered at two or more timed intervals during a day. Intervals between doses may be, for example, two doses administered approximately every 12 hours, or three doses administered approximately every 8 hours. Also as used herein a dose of Compound I refers to a unit dose of Compound I, or a pharmaceutically acceptable salt thereof, but may also be applicable to a medicament, or composition or dosage form comprising said unit dose of Compound I, or a pharmaceutically acceptable salt thereof.

In one embodiment, a dose of Compound I or a pharmaceutically acceptable salt thereof, is administered to a subject within 24 hours or less, before a dose of the nephrotoxic drug substance is administered to the subject. In a further embodiment, a dose of Compound I is administered to a subject within about 6 hours or less; optionally within about 2 hours or less, before the nephrotoxic drug substances is administered to the subject.

In a specific embodiment, Compound I or a pharmaceutically acceptable salt thereof is administered to a subject within 24 hours or less, or within about 6 hours or less, before a dose of an aminoglycoside, e.g. gentamicin is administered to the subject.

In another embodiment, Compound I or a pharmaceutically acceptable salt thereof is administered to the subject after the onset of reduced renal functions. The onset of reduced renal functions may be characterized by, amongst other physiological markers, elevated levels of serum creatinine and/or blood urea nitrogen (BUN) and/or oliguria. In one embodiment, said onset of reduced renal function may be characterized by blood urea nitrogen levels of at least 1.5 to 3 times higher than baseline and/or serum creatinine levels of at least 1.5 to 3 times higher than baseline and/or oliguria. In one embodiment, the subject has reduced renal function characterized by serum creatinine and BUN levels at least 2 times higher than baseline.

The onset of reduced renal function may in one embodiment be due to exposure to a nephrotoxic drug substance. For example, a subject may during the course of the treatment with a nephrotoxic drug substance suddenly develop renal impairment or dysfunction due to accumulation (e.g. blood concentration or localization to specific kidney cells or tissue) of a nephrotoxic drug substance, i.e. exposure to a cumulative dose of the nephrotoxic drug substance. Co-morbidities to the disease or condition arising or worsening during the course of treatment with a nephrotoxic drug substance may contribute to an onset of reduced renal function, leading to acute kidney injury. In other embodiments, the onset of reduced renal function may be due to exposure to an endogenous nephrotoxin, for example as describe in any one of the above embodiments and under any of the above described conditions leading to build-up of endogenous nephrotoxin.

In one embodiment, a dose of Compound I, a pharmaceutically acceptable salt thereof or a medicament or pharmaceutical composition comprising a dose of Compound I or a pharmaceutically acceptable salt thereof is administered to a subject about 1 to 24 hours, optionally about 1 to 6 hours after the onset of reduced renal function, e.g. characterized by blood urea nitrogen levels of at least 1.5 to 3 times higher than baseline and/or serum creatinine levels of at least 1.5 to 3 times higher than baseline and/or oliguria. In another embodiment, Compound I is administered to a subject about 1 to 24 hours, optionally about 1 to 6 hours after the onset of reduced renal function characterized by blood urea nitrogen and serum creatinine levels at least 2 times higher than baseline.

In another embodiment, Compound I or a pharmaceutically acceptable salt thereof is administered to a subject, preferably a human subject, at a dose of about 0.001 to 5 mg/kg, or at a dose of about 0.001 to 10 mg/kg. Optionally, Compound I may be administered to a subject, preferably a human subject at a dose of about 0.1 to 5 mg/kg, or 0.1 to 10 mg/kg. Said dose amount refers to a single dose. A single dose may be administered more than once during a course of treatment. Dose amounts, if described in respect of any pharmaceutically acceptable salts of Compound I herein refer to Compound I equivalents. A single dose of Compound I moreover, may be administered to a subject by administering a composition or medicament provided in a pharmaceutically acceptable dosage form, and comprising a dose of Compound I.

When used herein the term 'about' or the like in connection with an attribute or value such as dose amount includes the exact attribute or precise value, as well as any attribute or value typically considered to fall within the normal or accepted variability associated with the technical field, and methods of measuring or determining said attribute or value. The term allows for any variation which in the common practice would allow for the product being evaluated to be considered bioequivalent in a mammal to the recited strength or dose of a claimed product.

In a further aspect, the present disclosure provides for Compound I or a pharmaceutically acceptable salt thereof for use in the prevention and/or reduction of blood urea nitrogen levels of at least 1.5 to 3 times higher than baseline and/or serum creatinine levels of at least 1.5 to 3 times higher than baseline in a subject exposed to a nephrotoxin, e.g. a nephrotoxic drug substance or endogenous nephrotoxin, such as defined in any one of the above embodiments or combinations of embodiments.

In a further embodiment, Compound I or a pharmaceutically acceptable salt thereof is used for the prevention, or for the reduction of blood urea nitrogen and serum creatinine levels at least 2 times higher than baseline in a subject exposed to a nephrotoxin, wherein the nephrotoxin is a nephrotoxic drug substance (e.g. gentamicin, or any one or combination of substances described herein). In yet a further embodiment, Compound I or a pharmaceutically acceptable salt thereof is used for the prevention and/or reduction of reduction of blood urea nitrogen and serum creatinine levels at least 1.5 to 3 times higher than baseline in a subject exposed to a nephrotoxin, wherein the nephrotoxin is an aminoglycoside antibiotic, preferably gentamicin.

In another embodiment, Compound I or a pharmaceutically acceptable salt thereof is used for the reduction of blood urea nitrogen and/or serum creatinine levels in a subject exposed to a nephrotoxic drug substance (e.g. gentamicin) or an endogenous nephrotoxin, optionally wherein the blood urea nitrogen and/or serum creatinine level is reduced after administration of a dose, e.g. a first dose of Compound I. The reduction of BUN and serum creatinine may be determined by comparing BUN and serum creatinine values measured, using methods established in the art, prior to, and after administration of a (e.g. first) dose of Compound I.

The use of Compound I or a pharmaceutically acceptable salt thereof and method of treatment or prevention as described in any one of the embodiments herein is also provided in the context of the present disclosure, for the manufacture or preparation of a medicament or medicine adapted and prescribed for said uses or methods of treatment or prophylaxis.

A pharmaceutically acceptable salt of Compound I is a salt which retains its biological properties and which is non-toxic and is compatible for pharmaceutical use. Salts of the invention may result from the addition of acids to the Compound I. The resultant acid addition salts include those formed with acetic, 2,2 dichloroacetic, citric, lactic, mandelic, glycolic, adipic, alginic, aryl sulfonic acids (e.g., benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-aminosalicylic, sebacic, stearic, succinic, sulfuric, tannic, tartaric (e.g. (+)-L-tartaric), thiocyanic, undecylenic and valeric acids. In particular acid addition salts include those derived from mineral acids such as hydrochloric, hydrobromic, phosphoric, metaphosphoric, nitric and sulfuric acids; from organic acids, such as tartaric, acetic, citric, malic, lactic, fumaric, benzoic, glycolic, gluconic, succinic, arylsulfonic acids.

Compound I or a pharmaceutically acceptable salt thereof may be administered enterally or parenterally to a subject. In one embodiment, Compound I, or a composition or a medicament comprising said Compound I is adapted for administration or is administered parenterally, for example by intravenous injection or by sub-cutaneous, or intramuscular injection, or by intravenous or subcutaneous infusion. In an alternative embodiment, Compound I, or a composition or medicament comprising Compound I is adapted for administration, or is administered to a subject enterally, for example orally.

The present invention may also relate to a medicament, or a pharmaceutical composition comprising a Compound I or a pharmaceutically acceptable salt thereof according to any one or combination of the embodiments described herein above, and one or more pharmaceutically acceptable excipients. The medicament, or pharmaceutical composition comprising said Compound I may be formulated in a dosage form suitable or adapted for injection or infusion by any of the administration methods above. Alternatively, for oral administration, the medicament or pharmaceutical composition comprising Compound I may be provided in a dosage form suitable or adapted for oral administration, for example such as, but not limited to a tablet, capsule, gelcap, or film. Said medicament, or pharmaceutical composition may be used in accordance with any of the methods of treatment or prevention, or uses described herein.

In one embodiment, wherein Compound I is formulated in a dosage form suitable or adapted for injection or infusion, the formulation may be provided in the form of a clear solution, or as a lyophilized or freeze-dried powder, from which a clear solution may be obtainable, by reconstitution in a solvent or solution suitable, i.e. formulated for reconstitution. In one embodiment, said reconstitution solvent may comprise a solubilizer and/or a surfactant. In one specific embodiment, the reconstitution solution may comprise a polysorbate, e.g. polysorbate 80 or Tween 80; further optionally said solvent has a pH of between 3.5 and 4.5, or a pH between 4.2-4.5. In another embodiment, a medicament, or a pharmaceutical composition comprising Compound I or a pharmaceutically acceptable salt thereof may further comprise a polysorbate. The composition, in one embodiment, is a clear aqueous solution, with a pH between 3.5 and 4.5. In another embodiment, the solution has a pH between 4.2 and 4.5. In yet another embodiment, the composition comprising Compound I or a salt there of further comprises a polysorbate and optionally one or more further excipients, for example wherein the excipient is an acid (e.g. an organic acid) and/or one or more buffering agents. The polysorbate (e.g. a polyoxyethylene sorbitan monoester) is in one embodiment, polysorbate 80, or Tween 80 (polyoxyethylene sorbitan monooleate). In one embodiment, the composition comprises, or consists of an effective amount of Compound I or a salt thereof; a polysorbate, acetic acid, and an acetate salt, e.g. sodium acetate.

In another embodiment, Compound I is formulated with suitable acid. For example, Compound I may be formulated with an acid selected from succinic acid, L-malic acid or phosphoric acid. In yet a further embodiment, a composition comprising Compound I may further comprise a solubilizer and/or a surfactant, such as a polyethylene glycol, e.g. PEG 400, or a polysorbate e.g. Tween 80. In one specific embodiment, a composition comprising Compound I may further comprise of an acid e.g. succinic acid, L-malic acid, phosphoric acid or acetic acid, and a surfactant and/or a solubilizer, such as polyethylene glycol, e.g. PEG 400, or a polysorbate, e.g. Tween 80. The composition may, in one embodiment, be suitable or adapted for bolus injection, and may be provided in the form of a clear aqueous solution with pH between 5.4-5.6.

Compositions which are suitable for injection or infusion are generally in the form of solutions, meaning that formulation components, including active ingredients, must be fully dissolved or solubilized. The formation or presence of micellar phases or any other type of phase separation of any one of the components or active ingredient is not preferred, either at point of administration, or optionally, if the composition is stored as a solution, during storage. In one embodiment, a composition according to the present disclosure as described herein, and comprising Compound I or a salt thereof, is in the form of a clear solution. Preferably, the solution composition is in the form of a stable and clear solution, e.g. stable for at least 1 hour, or at least 15 hours at room temperature (or in cold storage such as at 0° C.). The stability of a solution may, for example be determined by visual inspection (e.g. for phase separation or other visible changes), or additionally, based on turbidity detector measurements.

Optionally, the medicament, or pharmaceutical composition comprising Compound I or a pharmaceutically acceptable salt thereof may also further comprise a drug substance, e.g. a nephrotoxic drug substance, i.e. Compound I may be co-formulated as a single composition or dosage form together with a nephrotoxic drug substance such as defined herein. Optionally, Compound I may be provided in a pharmaceutical composition further comprising gentamicin.

The present invention may in a further aspect, also relate to a kit comprising a composition comprising Compound I or a pharmaceutically acceptable salt thereof, and a composition comprising a nephrotoxic drug substance as described in any one of the embodiments herein, and optionally instructions for the administration of Compound I or a salt thereof as described in any one of the methods or uses described herein. Optionally, the kit may comprise a composition comprising Compound I or a pharmaceutically acceptable salt thereof and a nephrotoxic drug substance as described in any one of the embodiments here, e.g. gentamicin.

The following list of numbered items are embodiments comprised in the present disclosure:

1. Use of Compound I or a pharmaceutically acceptable salt thereof

Compound I

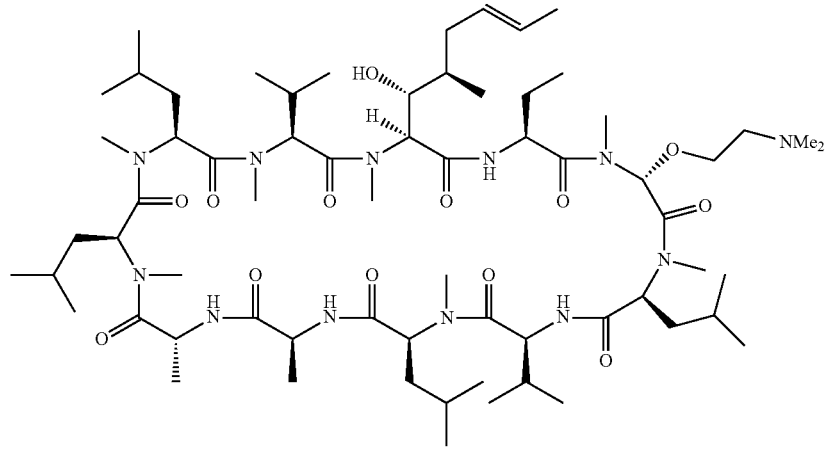

in the manufacture of a medicament for the prevention and/or treatment of a kidney condition or disease in a subject exposed to a nephrotoxin capable of inducing said kidney condition or disease, wherein the nephrotoxin is a nephrotoxic drug substance or an endogenous nephrotoxin.

2. The use according to item 1, wherein the nephrotoxic drug substance is selected from the group consisting of antimicrobial agents, cancer chemotherapeutic agents, blood pressure medicines including ACE inhibitors and angiotensin receptor blockers, macrolactone immunosuppressive agents, HIV protease inhibitors, peptic ulcer medicines, non-steroidal anti-inflammatory drugs, proton pump inhibitors, laxatives and contrast agents.

3. The use according to item 2, wherein the chemotherapeutic agent is selected from the group consisting of platins (e.g. carboplatin, cisplatin, oxaliplatin or nedaplatin), anthracyclines (e.g. daunorubicin, doxorubicin, idarubicin, epirubicin), bleomycins, mitomycins, actinomycins, cyclophosphamides, cytarabine, capecitabine, gemcitabine, ifosfamide, interleukin-2, streptozocin, gemtuzumab ozogamicin, melphalan, methotrexate, pemetrexed, plicamycin, and trimetrexate.

4. The use according to item 3, wherein the subject is undergoing cancer treatment, wherein said cancer treatment comprises the administration of the chemotherapeutic agent to the subject.

5. The use according to item 2, wherein the antimicrobial agent is selected from the group consisting of, aminoglycosides (e.g. gentamicin, tobramycin, amikacin, netilmicin, apramicin, streptomycin, kanamycin, neomycin, sisomycin), beta-lactams (e.g tazobactam, or piperacillin/tazobactam), polypeptide antibiotics (e.g. polymyxins such as polymyxin A, B, C, D, E (colistin), glycopeptide antibiotics (e.g. vancomycin), outer membrane protein targeting antibiotics, (e.g. murepavadin), antifungal agent (e.g. amphotericin B) and combinations thereof.

6. The use according to item 5, wherein the antimicrobial agent is gentamicin.

7. The use according to item 5 wherein the antimicrobial agent is murepavadin

8. The use according to any one of items 5 to 7, wherein the subject is suffering from an infection, and wherein said infection is treated by administering the antimicrobial agent to the subject.

9. The use according to item 2, wherein the blood pressure medicine is an ACE inhibitor, optionally selected from the group consisting of captopril, benazepril, enalapril, fosinopril, and ramipril; or an angiotensin receptor blocker, optionally selected from the group consisting of candesartan, valsartan, irbesartan, olmesartan, telmisartan, eprosartan, and losartan.

10. The use according to item 2, wherein the HIV protease inhibitor is selected from the group consisting of indinavir and ritonavir.

11. The use according to item 2, wherein the peptic ulcer medicine is selected from the group consisting of cimetidine, esomeprazole, lansoprazole, omeprazole, pantoprazole, and rabeprazole.

12. The use according to item 2, wherein the non-steroidal anti-inflammatory drug is selected from the group consisting of ibuprofen, ketoprofen, diclofenac, and aspirin.

13. The use according to item 2, wherein the laxative is selected from sodium phosphate.

14. The use according to item 2, wherein the nephrotoxic drug substance is a contrast agent, optionally an iodinated contrast agent (e.g. iothalamate, or iodixanol, or iohexol).

15. The use according to item 1, wherein the endogenous nephrotoxin is myoglobin.

16. The use according to item 15 wherein the subject has a creatine phosphokinase serum level of at least 5 times greater than baseline.

17. The use according to any one of items 15 or 16, wherein the subject has experienced or is suffering from physical trauma or crush injury, exposure to electrical current, extreme physical exertion or activity, and temperature extremes.
18. The use according to any one of items 1 to 17, wherein the medicament is administered to the subject prior to exposure to, or engagement with activities (e.g. extreme physical activity) associated with or at risk for onset of rhabdomyolysis.
19. The use according to any one of the preceding items, wherein the nephrotoxic drug substance is administered to the subject repeatedly.
20. The use according to item 19, wherein the nephrotoxic drug substance is administered at least twice, optionally at least once daily over a period of at least 3 days, or 7 days.
21. The use according to any one of the preceding items, wherein the kidney condition or disease is nephrotoxin-induced acute kidney injury or kidney failure, or wherein the kidney condition or disease is an aminoglycoside-induced acute kidney injury, e.g. gentamicin-induced acute kidney injury; or wherein the kidney condition disease is cisplatin-induced acute kidney injury.
22. The use according to any one of items 1 to 21, wherein the kidney condition or disease is selected from rhabdomyolysis, hemolysis, myoglobinuria, or optionally tumour lysis or myeloma-induced acute kidney injury.
23. The use according to any one of the preceding items, wherein the subject has a pre-existing condition or disease that increases the subject's risk of developing a kidney condition or disease when exposed to the nephrotoxin.
24. The use according to item 23, wherein the subject has a pre-existing kidney condition or disease, optionally wherein said pre-existing kidney condition is chronic kidney disease; optionally wherein the subject has a history of renal impairment or requires dialysis.
25. The use according to item 23 or 24, wherein the subject has reduced renal function, optionally wherein the subject has blood urea nitrogen levels of at least 1.5 to 3 times higher than baseline, and/or serum creatinine levels at least 1.5 to 3 times higher than baseline, and/or oliguria.
26. The use according to any one of the preceding items, wherein the medicament is administered to the subject prior to the subject's exposure to the nephrotoxic drug substance.
27. The use according to item any one of the preceding items, wherein a dose of the medicament is administered to the subject within 24 hours or less before a dose of the nephrotoxic drug substance is administered to the subject.
28. The use according to item 27, wherein a dose of the medicament is administered to the subject within about 6 hours or less, and optionally within about 2 hours or less, before the nephrotoxic drug substance is administered to the subject.
29. The use according to any one of the preceding items, wherein the medicament is administered to the subject after the onset of reduced renal functions as characterized by any one or combination of: blood urea nitrogen levels of at least 1.5 to 3 times higher than baseline, serum creatinine levels of at least 1.5 to 3 times higher than baseline, and oliguria.
30. The use according to item 29, wherein a dose of the medicament is administered to the subject 1 to 24 hours; optionally 1-6 hours, after the onset of reduced renal function.
31. The use according to any one of the preceding items, wherein the medicament is administered repeatedly to a subject during a first period of time which commences before and overlaps with a second period of time wherein the subject is exposed to repeatedly to the nephrotoxic drug substance.
32. The use according to any one of the preceding items, wherein the medicament is administered to the subject at a dose of about 0.001 to 10 mg/kg, and optionally about 0.1 to 10 mg/kg.
33. The use according to any one of the preceding items, wherein the subject is a human subject.
34. The use according to any one of the preceding items, wherein the medicament is formulated for administration by infusion or by injection, preferably subcutaneous, intramuscular or intravenous injection or intravenous or subcutaneous infusion.
35. Use of Compound I or a pharmaceutically acceptable salt thereof as defined in item 1 in the manufacture of a medicament for the prevention and/or reduction of blood urea nitrogen levels of at least 1.5 to 3 times higher than baseline and/or serum creatinine levels of at least 1.5 to 3 times higher than baseline in a subject exposed to a nephrotoxin.
36. The use according to item 35, wherein the nephrotoxin is as defined in any one of items 1 to 3, 5 to 7, or items 9 to 15, optionally wherein the subject exposed to said nephrotoxin has a kidney condition or disease induced by exposure to said nephrotoxin, e.g. a kidney condition or disease as defined in any one of items 21 or 22.
37. The use according to item 35 or 36, wherein the subject is defined as in any one of items 1, 4, 8, 16 to 17, 23 to 25 or 33.
38. The use according to items 35 to 37, wherein the medicament is administered as defined in any one of items 18 to 22, 26 to 32.
39. The use according to items 35 to 38, wherein the medicament is formulated for administration by injection or infusion, preferably intravenous injection or infusion.

40. Compound I, or a pharmaceutically acceptable salt thereof

Compound I

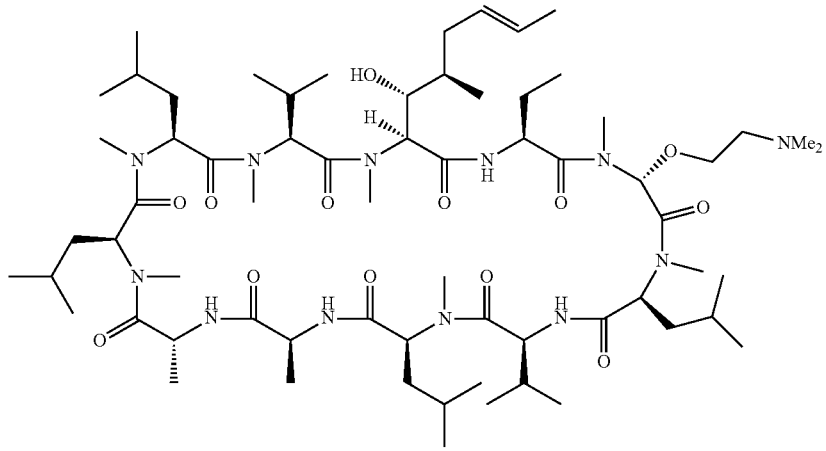

for use in the prevention and/or treatment of a kidney condition or disease in a subject exposed to a nephrotoxin capable of inducing said kidney condition or disease, wherein the nephrotoxin is a nephrotoxic drug substance or an endogenous nephrotoxin.

41. The compound for use according to item 40, wherein the nephrotoxic drug substance is selected from the group consisting of antimicrobial agents, cancer chemotherapeutic agents, blood pressure medicines including ACE inhibitors and angiotensin receptor blockers, macrolactone immunosuppressive agents, HIV protease inhibitors, peptic ulcer medicines, non-steroidal anti-inflammatory drugs, proton pump inhibitors, laxatives and contrast agents.

42. The compound for use according to item 41, wherein the chemotherapeutic agent is selected from the group consisting of platins (e.g. carboplatin, cisplatin, oxaliplatin or nedaplatin), anthracyclines (e.g. daunorubicin, doxorubicin, idarubicin, epirubicin), bleomycins, mitomycins, actinomycins, cyclophosphamides, capecitabine, cytarabine, gemcitabine, ifosfamide, interleukin-2, streptozocin, gemtuzumab ozogamicin, melphalan, methotrexate, pemetrexed, plicamycin, and trimetrexate.

43. The compound for use according to item 42, wherein the subject is undergoing cancer treatment, wherein said cancer treatment comprises the administration of the chemotherapeutic agent to the subject.

44. The compound for use according to item 41, wherein the antimicrobial agent is selected from the group consisting of, aminoglycosides (e.g. gentamicin, tobramycin, amikacin, netilmicin, apramicin, streptomycin, kanamycin, neomycin, sisomycin), beta-lactams (e.g tazobactam, or piperacillin/tazobactam), polypeptide antibiotics (e.g. polymyxins such as polymyxin A, B, C, D, E (colistin), glycopeptide antibiotics (e.g. vancomycin), outer membrane protein targeting antibiotics, (e.g. murepavadin), antifungal agent (e.g. amphotericin B) and combinations thereof.

45. The compound for use according to item 44, wherein the antimicrobial agent is an aminoglycoside antibiotic, preferably gentamicin.

46. The compound for use according to item 44 wherein the antimicrobial agent is murepavadin.

47. The compound for use according to any one of items 44 to 46, wherein the subject is suffering from an infection, and wherein said infection is treated by administering the antimicrobial agent to the subject.

48. The compound for use according to item 41, wherein the blood pressure medicine is an ACE inhibitor, optionally selected from the group consisting of captopril, benazepril, enalapril, fosinopril, and ramipril; or an angiotensin receptor blocker, optionally selected from the group consisting of candesartan, valsartan, irbesartan, olmesartan, telmisartan, eprosartan, and losartan.

49. The compound for use according to item 41, wherein the HIV protease inhibitor is selected from the group consisting of indinavir and ritonavir.

50. The compound for use according to item 41, wherein the peptic ulcer medicine is selected from the group consisting of cimetidine, esomeprazole, lansoprazole, omeprazole, pantoprazole, and rabeprazole.

51. The compound for use according to item 41, wherein the non-steroidal anti-inflammatory drug is selected from the group consisting of ibuprofen, ketoprofen, diclofenac, and aspirin.

52. The compound for use according to item 41, wherein the laxative is selected from sodium phosphate.

53. The compound for use according to item 41, wherein the nephrotoxic drug substance is a contrast agent, optionally an iodinated contrast agent (e.g. iothalamate, or iodixanol, or iohexol).

54. The compound for use according to item 40, wherein the endogenous nephrotoxin is myoglobin.

55. The compound for use according to item 54 wherein the subject has a creatine phosphokinase serum level of at least 5 times greater than baseline.

56. The compound for use according to any one of items 54 or 55 wherein the subject has experienced or is suffering from physical trauma or crush injury, exposure to electrical current, extreme physical exertion or activity, and temperature extremes.

57. The compound for use according to any one of items 40 to 56, wherein the compound is administered to the subject prior to exposure to, or engagement with activi- 58. The compound for use according to any one of items 40 to 57, wherein the nephrotoxic drug substance is administered to the subject repeatedly.
59. The compound for use according to item 58, wherein the nephrotoxic drug substance is administered at least twice, optionally at least once daily over a period of at least 3 days, or 7 days.
60. The compound for use according to any one of items 40 to 59, wherein the kidney condition or disease is nephrotoxin-induced acute kidney injury or kidney failure.
61. The compound for use according to any one of items 40 to 60, wherein the kidney condition or disease is selected from rhabdomyolysis, hemolysis, myoglobinuria, or optionally tumour lysis or myeloma-induced acute kidney injury.
62. The compound for use according to any one of items 60 or 61, wherein the kidney condition or disease is an aminoglycoside-induced acute kidney injury, preferably gentamicin-induced acute kidney injury.
63. The compound for use according to any one of the items 40 to 60, wherein the kidney condition or disease is cisplatin-induced acute kidney injury.
64. The compound for use according to any one of items 40 to 63, wherein the subject has a pre-existing condition or disease that increases the subject's risk of developing a kidney condition or disease when exposed to the nephrotoxin.
65. The compound for use according to item 64, wherein the subject has a pre-existing kidney condition or disease, optionally wherein said pre-existing kidney condition is chronic kidney disease; further optionally wherein the subject has a history of renal impairment or requires dialysis.
66. The compound for use according to item 64 or 65, wherein the subject has reduced renal function, optionally wherein the subject has one or a combination of: blood urea nitrogen level at least 1.5 to 3 times higher than baseline, serum creatinine levels at least 1.5 to 3 times higher than baseline, or oliguria.
67. The compound for use according to any one of items 40 to 66, wherein the compound or a pharmaceutically acceptable salt thereof is administered to the subject prior to the subject's exposure to the nephrotoxic drug substance.
68. The compound for use according to any one of items 40 to 67, wherein a dose of Compound I or a pharmaceutically acceptable salt thereof is administered to the subject within 24 hours or less before a dose of the nephrotoxic drug substance is administered to the subject.
69. The compound for use according to item 68, wherein a dose of Compound I or a pharmaceutically acceptable salt thereof is administered to the subject within about 6 hours or less, and optionally within about 2 hours or less, before the nephrotoxic drug substance is administered to the subject.
70. The compound for use according to any one of items 40 to 69, wherein the compound is administered to the subject after the onset of reduced renal functions as characterized by any one or combination of: a blood urea nitrogen level of at least 1.5 to 3 times higher than baseline, serum creatinine level at least 1.5 to 3 times higher than baseline, and oliguria.
71. The compound for use according to item 70, wherein a dose of Compound I or a pharmaceutically acceptable salt thereof is administered to the subject 1 to 24 hours; optionally 1 to 6 hours, after the onset of reduced renal function as defined in item 70.
72. The compound for use according to any one of items 40 to 71, wherein the compound is administered repeatedly to a subject during a first period of time which commences before and overlaps with a second period of time wherein the subject is exposed to repeatedly to the nephrotoxic drug substance.
73. The compound for use according to any one of items 40 to 72, wherein the compound is administered to the subject at a dose of about 0.001 to 10 mg/kg, and optionally about 0.1 to 10 mg/kg.
74. The compound for use according to any one of items 40 to 73, wherein the subject is a human subject.
75. The compound for use according to any one of items 40 to 74, wherein the compound is formulated for administration by infusion or by injection, preferably subcutaneous, intramuscular or intravenous injection or intravenous or subcutaneous infusion.
76. Compound I or a pharmaceutically acceptable salt thereof as defined in item 40 for use in the prevention and/or the reduction of blood urea nitrogen levels of at least 1.5 to 3 times higher than baseline and/or serum creatinine levels of at least 1.5 to 3 times higher than baseline in a subject exposed to a nephrotoxin.
77. The compound for use according to item 76, wherein the nephrotoxin is as defined in any one of items 40 to 42, 44 to 46, or items 48 to 54, optionally wherein the subject exposed to said nephrotoxin has a kidney condition or disease induced by exposure to said nephrotoxin, e.g. a kidney condition or disease as defined in any one of items 60 to 63.
78. The compound for use according to item 76 or 77, wherein the subject is defined as in any one of items 43, 47, 55 to 56, 64 to 66, or 74.
79. The compound for use according to items 76 to 78, wherein the compound or pharmaceutically acceptable salt thereof is administered as defined in any one of items 57 to 59, or items 67 to 73.
80. The compound for use according to items 76 to 79, wherein the compound or pharmaceutically acceptable salt thereof is administered by injection or infusion, preferably intravenous injection or infusion.
81. A method for preventing and/or treating a kidney condition or disease in a subject exposed to a nephrotoxin capable of inducing said kidney condition or disease, wherein the nephrotoxin is a nephrotoxic drug substance or an endogenous nephrotoxin and wherein the method comprises administering to said subject Compound I, or a pharmaceutically acceptable salt thereof

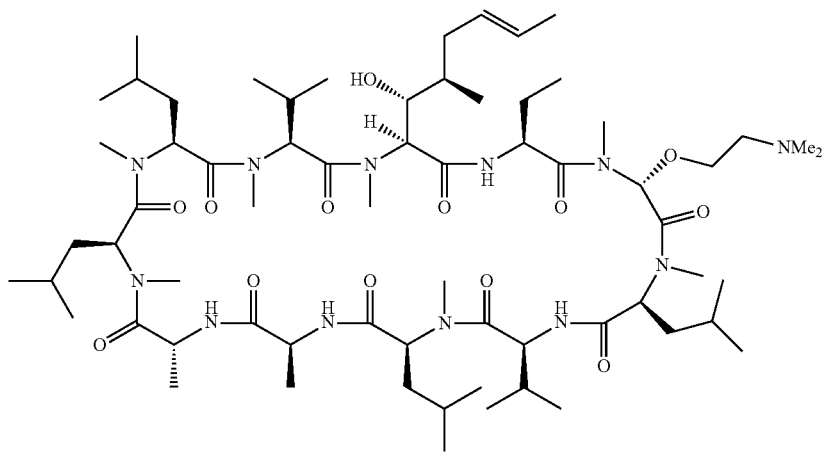

Compound I

82. The method according to item 81, wherein the nephrotoxic drug substance is selected from the group consisting of antimicrobial agents, cancer chemotherapeutic agents, blood pressure medicines including ACE inhibitors and angiotensin receptor blockers, macrolactone immunosuppressive agents, HIV protease inhibitors, peptic ulcer medicines, non-steroidal anti-inflammatory drugs, proton pump inhibitors, laxatives and contrast agents.
83. The method according to item 82, wherein the chemotherapeutic agent is selected from the group consisting of platins (e.g. carboplatin, cisplatin, oxaliplatin or nedaplatin), anthracyclines (e.g. daunorubicin, doxorubicin, idarubicin, epirubicin), bleomycins, mitomycins, actinomycins, cyclophosphamides, capecitabine, cytarabine, gemcitabine, ifosfamide, interleukin-2, streptozocin, gemtuzumab ozogamicin, melphalan, methotrexate, pemetrexed, plicamycin, and trimetrexate.
84. The method according to item 83, wherein the subject is undergoing cancer treatment, wherein said cancer treatment comprises the administration of the chemotherapeutic agent to the subject.
85. The method according to item 82, wherein the antimicrobial agent is selected from the group consisting of, aminoglycosides (e.g. gentamicin, tobramycin, amikacin, netilmicin, apramicin, streptomycin, kanamycin, neomycin, sisomycin), beta-lactams (e.g tazobactam, or piperacillin/tazobactam), polypeptide antibiotics (e.g. polymyxins such as polymyxin A, B, C, D, E (colistin), glycopeptide antibiotics (e.g. vancomycin), outer membrane protein targeting antibiotics, (e.g. murepavadin), antifungal agent (e.g. amphotericin B) and combinations thereof.
86. The method according to item 85, wherein the antimicrobial agent is an aminoglycoside antibiotic, preferably gentamicin.
87. The method according to item 85 wherein the antimicrobial agent is murepavadin.
88. The method according to any one of items 85 to 87, wherein the subject is suffering from an infection, and said infection is treated by administering the antimicrobial agent to the subject.
89. The method according to item 82, wherein the blood pressure medicine is an ACE inhibitor, optionally selected from the group consisting of captopril, benazepril, enalapril, fosinopril, and ramipril; or an angiotensin receptor blocker, optionally selected from the group consisting of candesartan, valsartan, irbesartan, olmesartan, telmisartan, eprosartan, and losartan.
90. The method according to item 82, wherein the HIV protease inhibitor is selected from the group consisting of indinavir and ritonavir.
91. The method according to item 82, wherein the peptic ulcer medicine is selected from the group consisting of cimetidine, esomeprazole, lansoprazole, omeprazole, pantoprazole, and rabeprazole.
92. The method according to item 82, wherein the non-steroidal anti-inflammatory drug is selected from the group consisting of ibuprofen, ketoprofen, diclofenac, and aspirin.
93. The method according to item 82, wherein the laxative is selected from sodium phosphate.
94. The method according to item 82, wherein the nephrotoxic drug substance is a contrast agent, optionally an iodinated contrast agent (e.g. iothalamate, or iodixanol, or iohexol).
95. The method according to item 81, wherein the endogenous nephrotoxin is myoglobin.
96. The method according to item 95 wherein the subject has a creatine phosphokinase serum level of at least 5 times greater than baseline.
97. The method according to any one of items 95 or 96 wherein the subject has experienced or is suffering from physical trauma or crush injury, exposure to electrical current, extreme physical exertion or activity, and temperature extremes.
98. The method according to any one of items 81 to 97, wherein Compound I or a pharmaceutically acceptable salt thereof is administered to the subject prior to exposure to, or engagement with activities (e.g. extreme physical activity) associated with, or at risk for onset of rhabdomyolysis.
99. The method according to any one of items 81 to 98, wherein the nephrotoxic drug substance is administered to the subject repeatedly.
100. The method according to item 99, wherein the nephrotoxic drug substance is administered at least twice, optionally at least once daily over a period of at least 3 days, or 7 days.

101. The method according to any one of items 81 to 100, wherein the kidney condition or disease is nephrotoxin-induced acute kidney injury or kidney failure.
102. The method according to any one of items 81 to 101, wherein the kidney condition or disease is selected from rhabdomyolysis, hemolysis, myoglobinuria, or optionally tumour lysis or myeloma-induced acute kidney injury.
103. The method according to any one of items 101 or 102, wherein the kidney condition or disease is an aminoglycoside-induced acute kidney injury, preferably gentamicin-induced acute kidney injury.
104. The method according to any one of the items 101 or 102, wherein the kidney condition or disease is cisplatin-induced acute kidney injury.
105. The method according to any one of items 81 to 104, wherein the subject has a pre-existing condition or disease that increases the subject's risk of developing a kidney condition or disease when exposed to the nephrotoxin.
106. The method according to item 105, wherein the subject has a pre-existing kidney condition or disease, optionally wherein said pre-existing kidney condition is chronic kidney disease; further optionally wherein the subject has a history of renal impairment or requires dialysis.
107. The method according to item 105 or 106, wherein the subject has reduced renal function, optionally wherein the subject has one or a combination of: blood urea nitrogen level at least 1.5 to 3 times higher than baseline, serum creatinine levels at least 1.5 to 3 times higher than baseline, or oliguria.
108. The method according to any one of items 81 to 107, wherein Compound I or a pharmaceutically acceptable salt thereof is administered to the subject prior to the subject's exposure to the nephrotoxic drug substance.
109. The method according to any one of items 81 to 108, wherein a dose of Compound I or a pharmaceutically acceptable salt thereof is administered to the subject within 24 hours or less before a dose of the nephrotoxic drug substance is administered to the subject.
110. The method according to item 109, wherein a dose of Compound I or a pharmaceutically acceptable salt thereof is administered to the subject within about 6 hours or less, and optionally within about 2 hours or less, before the nephrotoxic drug substance is administered to the subject.
111. The method according to any one of items 81 to 110, wherein Compound I or a pharmaceutically acceptable salt thereof is administered to the subject after the onset of reduced renal functions as characterized by any one or combination of: a blood urea nitrogen level of at least 1.5 to 3 times higher than baseline, serum creatinine level at least 1.5 to 3 times higher than baseline, and oliguria.
112. The method according to item 111, wherein a dose of Compound I or a pharmaceutically acceptable salt thereof is administered to the subject 1 to 24 hours; optionally 1 to 6 hours, after the onset of reduced renal function as defined in item 111.
113. The method according to any one of items 81 to 112, wherein Compound I or a pharmaceutically acceptable salt thereof is administered repeatedly to a subject during a first period of time which commences before and overlaps with a second period of time wherein the subject is exposed to repeatedly to the nephrotoxic drug substance.
114. The method according to any one of items 81 to 113, wherein Compound I or a pharmaceutically acceptable salt thereof is administered to the subject at a dose of about 0.001 to 10 mg/kg, and optionally about 0.1 to 10 mg/kg.
115. The method according to any one of items 81 to 114, wherein the subject is a human subject.
116. The method according to any one of items 81 to 115, wherein Compound I or a pharmaceutically acceptable salt thereof is administered by infusion or by injection, preferably subcutaneous, intramuscular or intravenous injection or intravenous or subcutaneous infusion.
117. A method for preventing and/or reducing blood urea nitrogen levels of at least 1.5 to 3 times higher than baseline and/or serum creatinine levels of at least 1.5 to 3 times higher than baseline in a subject exposed to a nephrotoxin (e.g. a nephrotoxic drug substance or an endogenous nephrotoxin), the method comprising administering to said subject Compound I or a pharmaceutically acceptable salt thereof as defined in item 81.
118. The method according to item 117, wherein the nephrotoxin is as defined in any one of items 81 to 83, 85 to 87, or items 89 to 95.
119. The method according to item 117 or 118, wherein the subject is defined as in any one of items 84, 88, 96 to 97, 105 to 107, or 115.
120. The method according to items 117 to 119, wherein the compound or pharmaceutically acceptable salt thereof is administered as defined in any one of items 98 to 100, 108 to 114, or 116.
121. The method according to items 117 to 120, wherein the subject exposed to the nephrotoxin has a kidney condition or disease induced by exposure to the nephrotoxin, e.g. a kidney condition or disease as defined in any one of items 101 to 104.
122. The method according to items 117 to 121, wherein the compound or pharmaceutically acceptable salt thereof is administered by injection or infusion, preferably intravenous injection or infusion.
123. A pharmaceutical composition comprising Compound I or a pharmaceutically acceptable salt thereof, and one or more further excipients, optionally wherein the composition further comprises a polysorbate (e.g. polysorbate 80, or Tween 80).
124. The pharmaceutical composition according to item 123, wherein the composition is a clear aqueous solution with a pH between 3.5 and 4.5, or between 4.2 and 4.5.
125. The pharmaceutical composition according to items 123 to 124, wherein the composition further comprises acetic acid and/or an acetate salt.
126. A process for the preparation of a pharmaceutical composition according to item 123 to 125, comprising the steps of combining a lyophilized powder composition of Compound I or a salt thereof with a reconstitution solvent comprising polysorbate (e.g. polysorbate 80).
127. A pharmaceutical composition comprising Compound I or a pharmaceutically acceptable salt thereof (e.g. a succinic acid, L-malic acid or phosphoric acid salt), and one or more further excipients, optionally wherein the composition further comprises a polysorbate (e.g. polysorbate 80, or Tween 80) or a polyethylene glycol (e.g. PEG400).
128. The pharmaceutical composition according to item 127, wherein the composition is a clear aqueous solution with a pH between 5.4-5.6, optionally where the composition is adapted for, or is administered as a bolus injection.

129. The pharmaceutical composition according to items 123 to 128 for use according to any of the uses or methods of treatment and/or prophylaxis as defined in any one of items 1 to 122.

The following examples serve to illustrate the invention, however should not be understood as restricting the scope of the invention.

EXAMPLES

Example 1—Gentamicin-Induced Acute Kidney Injury Model in Rats

Efficacy of the compound of Compound I against gentamicin-induced acute kidney injury was tested in a model study with male Wistar rats (180-220 g) randomly grouped based on body weights. Three groups formed part of the study: control, vehicle, and compound I (see Table I). Except for the control group, gentamicin (100 mg/kg) was given by intraperitoneal injection for 10 consecutive days, once daily from Day 1 to Day 10. The first day of gentamicin injection was designated as Day 1 of the study.

TABLE I

| Group | Number of animals | Compound Treatment | Dose (mg/kg) | Dosing Volume | Dosing Route | Dosing Schedule |
|---|---|---|---|---|---|---|
| 1 | 8 | Control | — | — | — | — |
| 2 | 8 | Vehicle | — | 5 ml/kg | i.p. | 11 times in total |
| 3 | 8 | Compound I | 3 mg/kg | 5 ml/kg | i.p. | 11 times in total |

The vehicle, or the Compound I formulated in the vehicle was administered intraperitoneally (i.p.) for 10 days, from Day 1 to Day 10 of the study (total 11 times). On initiation of the experiment (Day 1), Compound I (3 mg/kg) was administered by i.p. injection 6 h, and 1 h before the gentamicin injection. Thereafter, on Day 2 to Day 10, Compound I was administered once daily (3 mg/kg) 1 h prior to the gentamicin injection. Body weights of the rats were recorded daily. On the day 10, the animals were euthanized and blood sample was collected via cardiac punction. Serum was collected and stored at −80° C. for kidney function analysis of blood urea nitrogen (BUN) and creatinine.

Results

Figure 1A:
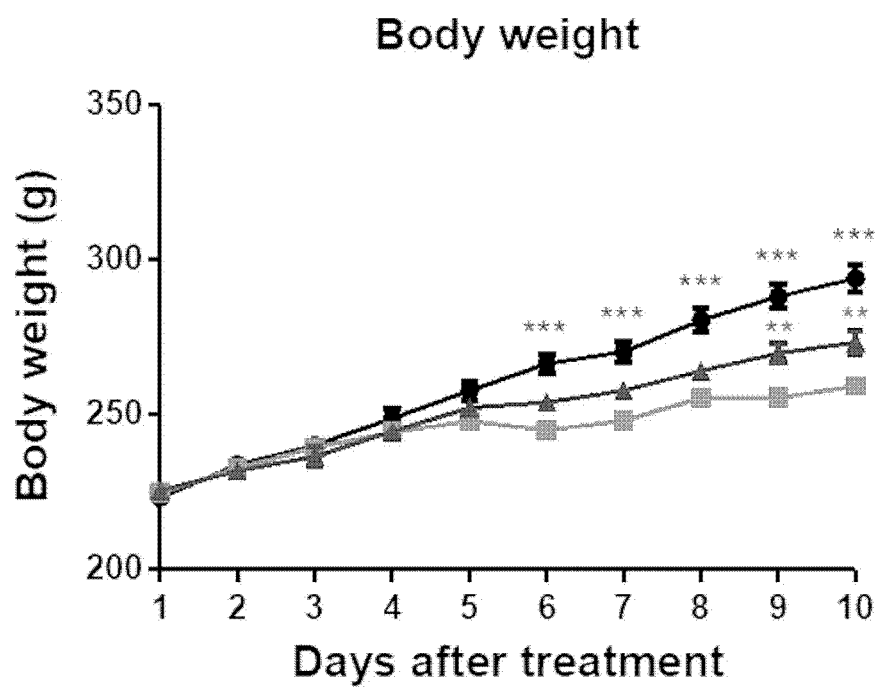
FIG. 1A is a graphical depiction of the average body weight of male Wistar rats as recorded over the 10-day period of the gentamicin-induced acute kidney injury study described in Example 1. The Control group (no treatment with gentamicin) is represented as circular dots, and the Vehicle group as squares and the Compound I group as triangles, respectively. The rats of the Vehicle group and the Compound I group were treated with Vehicle or Compound I (3 mg/kg), once a day i.p, respectively. Both of the Vehicle and the Compound I group were i.p gentamicin one dose per day for the acute kidney injury modelling.
Figure 1B:
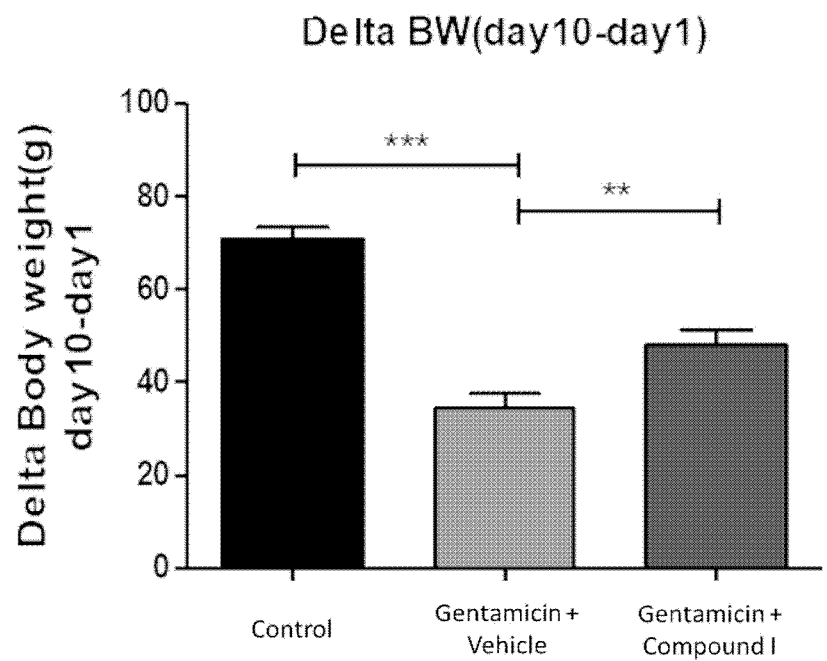
FIG. 1B depicts the delta body weight i.e. change from baseline (Day 1) to endpoint (Day 10) of the average body weight of male Wistar rats in the gentamicin-induced acute kidney injury study described in Example 1. Depicted from left to right on the x-axis are: the Control group (treatment without gentamicin); the Vehicle group (one dose per day vehicle and one dose per day gentamicin); the Compound I group (one dose per day after Day 1 of Compound I (dose amount: 3 mg/kg) in vehicle and one dose per day gentamicin).

Body Weight—Acute kidney injury has rapid impact on the growth/weight gain of Wistar rats. As depicted in FIG. 1A, it was observed that for the vehicle group (rats receiving only vehicle prior to gentamicin), the rate of body weight gain was slow over the 10-day study period. In contrast, a faster rate of body weight gain was for group treated with Compound I prior to being administered gentamicin. It was also observed, as depicted in FIG. 1B that the overall body-weight change from baseline measurement on Day 1 of the rats treated with Compound I was also higher compared to the rats only treated with vehicle.

Figure 2:
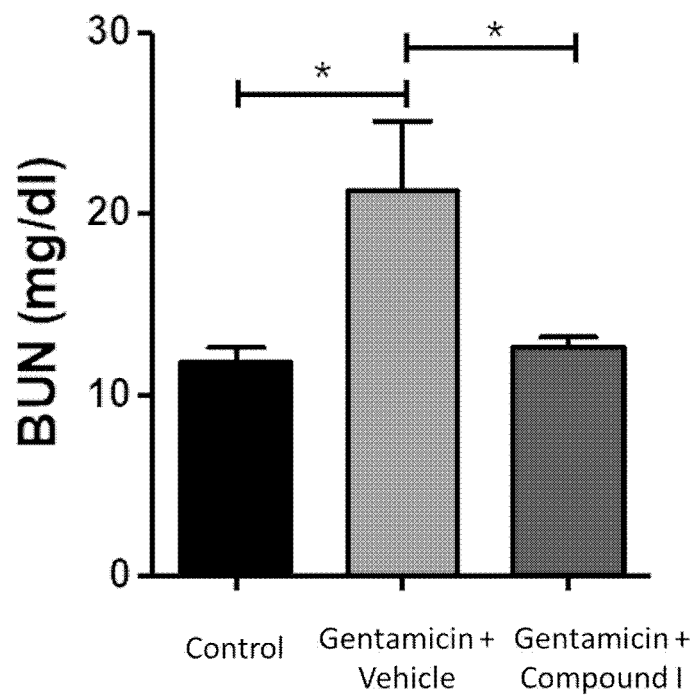
FIG. 2 depicts the study endpoint blood urea nitrogen (BUN) serum levels. Depicted from left to right on the x-axis are: the Control group (no treatment); the Vehicle group (one dose per day vehicle and one dose per day gentamicin); the Compound I group (one dose per day after Day 1 of Compound I (dose amount: 3 mg/kg) in vehicle and one dose per day gentamicin).
Figure 3:
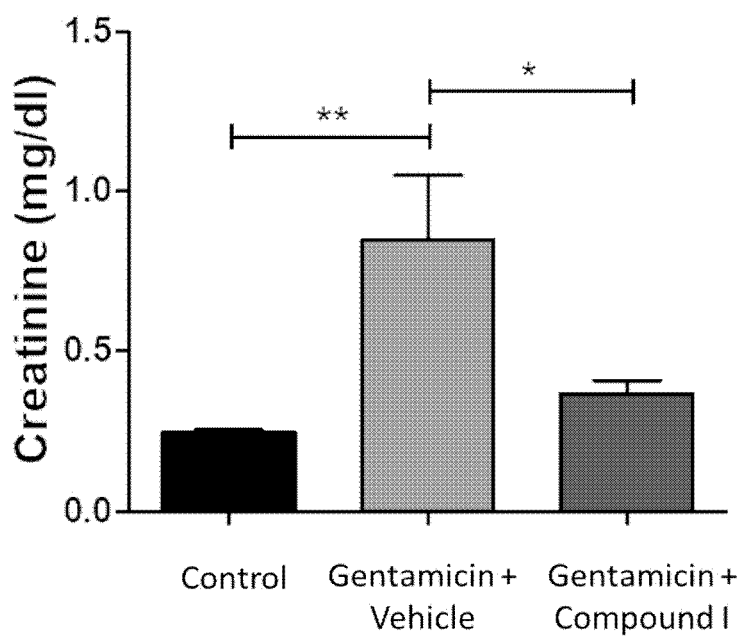
FIG. 3 depicts the study endpoint creatinine serum levels. Depicted from left to right on the x-axis are: the Control group (no treatment); the Vehicle group (one dose per day vehicle and one dose per day gentamicin); the Compound I group (one dose per day after Day 1 of Compound I (dose amount: 3 mg/kg) in vehicle and one dose per day gentamicin).

Blood Urea Nitrogen (BUN)/Creatinine Serum endpoint measurements (see FIGS. 2 and 3)—the rats receiving only vehicle and gentamicin had higher BUN and creatinine levels associated with acute kidney injury expected on the basis of high doses of gentamicin. In contrast, both serum BUN and creatinine levels in rats treated with Compound I and administered with gentamicin were lower, compared to levels determined for the vehicle group, despite receiving the same high doses of gentamicin. The serum levels were unexpectedly found to be at comparable or similar levels as measured for the control group where no gentamicin was administered, demonstrating that Compound I is efficacious in treating and preventing the increase of these renal function markers during exposure to gentamicin. This data illustrates the protective effects of Compound I against the toxicity of gentamicin.

Example 2—Gentamicin-Induced Acute Kidney Injury Model in Rats-Pathology Studies A further study in rats was carried out essentially in analogy to the general study protocol described in Example 1, to further assess the efficacy and impact of Compound I against gentamicin-induced acute kidney injury and to test the dose response. The tissue pathology, as well as the additional biomarkers were assessed.

Five groups formed part of the study (See Table 2): control (Group 1), vehicle (Group 2), and animals receiving Compound I at doses of 0.5 mg/kg (Group 3), 3 mg/kg (Group 4) and 9 mg/kg (Group 5). Except for the control Group 1, gentamicin (100 mg/kg) was given by intraperitoneal injection for 10 consecutive days, once daily from Day 1 to Day 10.

TABLE 2

| Group | Number of animals | Compound Treatment | Dose (mg/kg) | Dosing Volume | Dosing Route | Dosing Schedule |
|---|---|---|---|---|---|---|
| 1 | 8 | Control | — | — | — | — |
| 2 | 8 | Vehicle | — | 5 ml/kg | i.p. | 11 times in total |
| 3 | 8 | Compound I | 0.5 mg/kg | 5 ml/kg | i.p. | 11 times in total |
| 4 | 8 | Compound I | 3 mg/kg | 5 ml/kg | i.p. | 11 times in total |
| 5 | 8 | Compound I | 9 mg/kg | 5 ml/kg | i.p. | 11 times in total |

The vehicle, or Compound I formulated in the vehicle was administered intraperitoneally (i.p.) for 10 days, from Day 1 to Day 10 of the study (total 11 times). On initiation of the experiment (Day 1), Compound I at the specified dose amounts was administered by i.p. injection 6 h, and 1 h before the gentamicin injection to the animals in groups 3, 4 and 5. Thereafter, on Day 2 to Day 10, Compound I was administered once daily at the specified dose to said study groups, approximately 1 h prior to the gentamicin injection. On day 10, the rats were euthanized. Blood samples were collected, and the kidney tissues (both left and right kidneys) of the rats were also taken for H&E staining. Histopathological evaluation was performed on the kidney sections using standard methods and scoring criteria in the art to assess the level of tissue damage caused by the gentamicin-induced acute kidney injury. The kidney sections were assessed and scored for: necrosis of renal tubules, tubular dilation, loss of tubular brush border, cast formation in the renal tubules, and interstitial inflammatory cell (neutrophil) infiltration. The scoring was performed on a scale of 0 to 4 (0=0% i.e. no observation, 1≤5%, 2=5-25%, 3=25-50%, 4≥50% i.e. extensive, severe, or widely visible damage) on both left and right kidney tissues. The scoring was accumulated to provide a total combined score.

Kidney function analysis based on blood urea nitrogen (BUN) and creatinine in the serum was performed. Assay in plasma for biomarkers NGAL (neutrophil gelatinase-associated lipocalin) and Kim-1 (kidney injury molecule-1) was also determined. These biomarker proteins are typically upregulated in acute kidney injury and are useful as early indicators of acute kidney injury, e.g. such caused by exposure to nephrotoxins.

Results

Figure 4A:
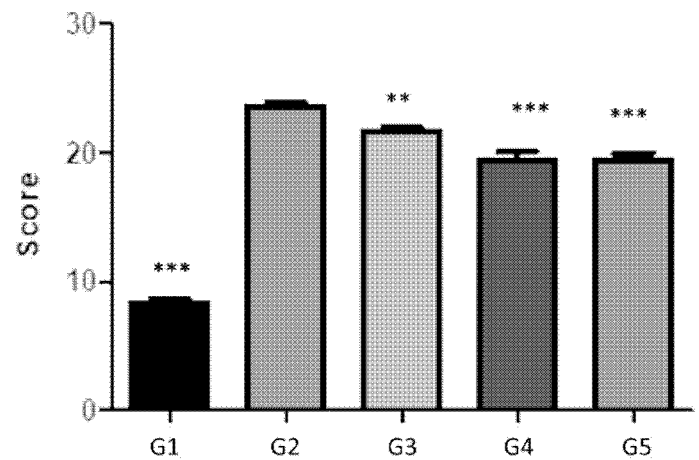
FIG. 4A depicts the total acute kidney injury pathology scoring for kidney tissue samples (left and right kidney tissue) obtained at endpoint of the model study of gentamicin-induced acute kidney injury as described in Example 2. Depicted from left to right on the x-axis are the total acute kidney injury scores for each of the study groups: G1 (Group 1, control; no treatment with gentamicin or Compound I); G2 (Group 2, one dose per day each of vehicle and gentamicin), G3 (Group 3), G4 (Group 4) and G5 (Group 5) were administered i.p Compound I, one dose per day of 0.5, 3 and 9 mg/kg respectively, and one dose per day of gentamicin.  refers to P<0.01;  refers to P<0.001 versus G2, based on one-way ANOVA; Dunnett's multiple comparison test.
Figure 4B:
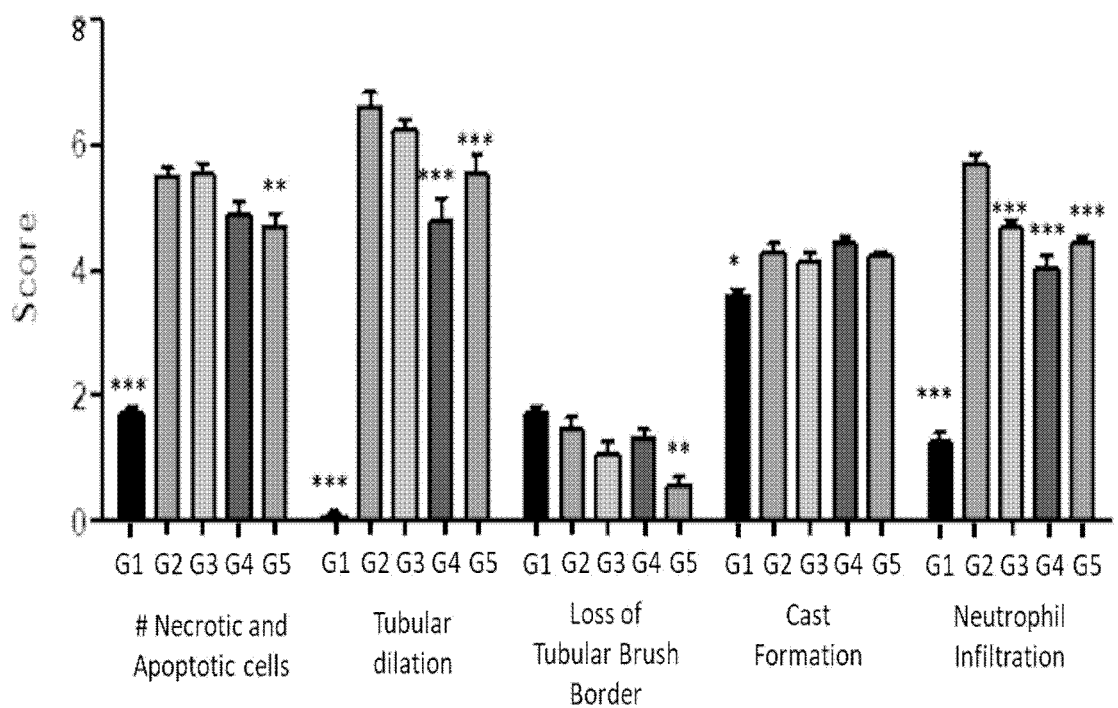
FIG. 4B depicts the scoring for acute kidney injury of kidney tissue samples (left and right kidney obtained at endpoint of the study of gentamicin-induced acute kidney injury as described in Example 2, for the specific kidney tissue pathologies which were assessed. Depicted are the scores for each of the groups G1-G5 as described for FIG. 4A. Depicted from left to right on the x-axis are the scoring for study groups G1-G5, in respect of the following acute kidney injury pathologies: the numbers of necrotic and apoptotic cells, tubular dilation, loss of tubular brush border, cast formation, and neutrophil infiltration * refers to P<0.05,  refers to P<0.01; * refers to P<0.001 versus G2 study group, based on two-way ANOVA; Bonferroni comparison test.

Histopathological Evaluation—It was observed (see FIG. 4A) that the administration of Compound I to rats in the gentamicin-induced acute kidney injury model, especially the 3 mg/kg and 9 mg/kg groups had a statistically significant impact in terms of generally reducing the severity of physical injury caused or induced by gentamicin in the kidney tissue of the rats compared to the model group (G2) receiving only vehicle in addition to gentamicin. FIG. 4B, which depicts the pathologies which were analyzed, also shows that the severity of injury pathologies particularly effected by gentamicin under the conditions of the model, such as tubular dilation, and neutrophil infiltration, are markedly reduced in the study groups receiving Compound I.

Serum Creatinine/Blood Urea Nitrogen (BUN) endpoint measurements (see FIGS. 5 and 6 respectively)—the rats receiving only vehicle and gentamicin (Group 2) had high BUN and creatinine levels associated with acute kidney injury expected on the basis of high doses of gentamicin. In contrast, both serum BUN and creatinine levels in rats treated with Compound I and gentamicin were lower despite receiving also same high dose levels of gentamicin.

KIM-1/NGAL biomarker endpoint measurements in plasma (see FIGS. 7 and 8 respectively)—these biomarkers may be considered more specific, as well as useful as earlier indicators of acute kidney injury. The rats receiving only vehicle and gentamicin (Group 2) were determined to have high levels of both of these biomarkers. In comparison to the model G2 group, it can be observed that statistically relevant reduced levels of these biomarkers were measured from the rat study groups receiving Compound I, especially study groups G4 and G5.

Example 3—Rhabdomyolysis-Induced Acute Kidney Injury Model in Rats

The efficacy of Compound I in protection against rhabdomyolysis-induced acute kidney injury was tested in a model study in male SD rats. The acute kidney injury model was induced in the rats by bilateral intra-muscular injection of 50% Glycerine (at a dose volume of 10 ml/kg body weight, divided into two sites of injection at each limb). Glycerine induces physiological conditions which are closely associated with rhabdomyolysis, such as myoglobinuria, tubular necrosis, and renal vasoconstriction.

Three groups formed part of the study: sham, vehicle, and compound I. Except for the sham group, where no glycerine was injected, animals were dosed twice intraperitoneally with either Compound I or Vehicle: at 6 h and at 1 h prior to receiving the glycerine injection (see Table 3).

TABLE 3

| Group No. | No. of Animals | Treatment | Route | Dose (mg/kg) | Dose Volume (ml/kg) | Dosing Regimen |
|---|---|---|---|---|---|---|
| 1 | n = 4 | Sham | NA | NA | NA | NA |
| 2 | n = 10 | Vehicle | IP | 0 | 5 | Twice: at 6 h and at 1 h prior to administration of Glycerine |
| 3 | n = 10 | Compound I | | 3 | 5 | |

After 48 h, the animals were euthanized, and their right and left kidneys were fixed in formalin 10%. Each kidney was cut longitudinally into 2 halves, both placed in a cassette and processed in paraffin. Sections were cut and stained using Hematoxylin and Eosin (H&E). The kidney sections were examined and histopathological analysis and scoring was performed for tubular, endothelial, glomerular and tubulointerstitial damage based on scoring systems in the art (e.g. Khalid U. et al, Journal of Histology & Histopathology. Volume 3, Article 1. 2016). Tubular epithelial necrosis scoring was based on the total number of tubules in the outer stripe of the outer medulla (OSOM). Tubulointerstitial damage was scored as a total percentage of the entire tissue observed in the section. The scores of each parameter were also added to provide a total histopathological score.

Results

The injection of glycerine was observed to induce mild-to-moderate necrosis of tubular epithelial cells in the outer stripe of the outer medulla (OSOM). The formation of protein casts and tubulointerstitial necrosis was mild. No endothelial or glomerular damage was found. These findings are compatible with transient ischemia as modeled by the study. The sham group, serving as a control, did not receive any glycerine injections. The mean score of tubular damage following glycerine injection showed statistically significant elevation in both vehicle and Compound I groups in comparison to the sham group which did not receive any glycerine injections (1.40±0.15 and 1.10±0.07 vs. 0.00±0.00 for Groups 2 and 3 vs. Group 1, respectively, p<0.01) The mean tubulo-interstitial damage score was also statistically significantly higher in both vehicle and Compound I groups in comparison to the sham group (2.00±0.00 and 1.15±0.08 vs. 0.00±0.00 for Groups 2 and 3 vs. Group 1, respectively, p<0.01). Consequently, the mean total histopathological score was also statistically significantly higher in both vehicle and Compound I groups in comparison to the sham group which did not receive glycerine (3.20±0.14 and 2.15±0.08 vs. 0.00±0.00 for Groups 2 and 3 vs. Group 1, respectively, p<0.01).

Table 4 summarizes the histopathology scoring results for the test groups sham (Group 1), vehicle (Group 2) and compound I (Group 3). All data are presented as Mean±SEM. All treatment groups were compared to the sham group (Group 1) or to the vehicle group (Group 2) using Student's T-Test. A p value <0.05 is considered to represent a significant difference.

TABLE 4

| Group No. | TD (a.u.) | | ED (a.u.) | | GD (a.u.) | | TID (a.u.) | | Total (a.u.) | |
|---|---|---|---|---|---|---|---|---|---|---|
| | Mean | SEM | Mean | SEM | Mean | SEM | Mean | SEM | Mean | SEM |
| 1 | 0.00 | 0.00 | 0.00 | 0.00 | 0.00 | 0.00 | 0.00 | 0.00 | 0.00 | 0.00 |
| 2 | 1.40## | 0.15 | 0.00 | 0.00 | 0.00 | 0.00 | 2.00## | 0.00 | 3.20## | 0.14 |
| 3 | 1.10## | 0.07 | 0.00 | 0.00 | 0.00 | 0.00 | 1.15##** | 0.08 | 2.15##** | 0.08 |

TD = Tubular Damage;
ED = Endothelial damage,
GD = Glomerular damage;
TID = Tubulointersititial damage,
Total = Total Histopathological Score
**p <0.01 vs. vehicle (Group 2) using Student's T-test
p <0.01 vs. sham (Group 1) using Student's T-test Injection of Compound I prior to onset of glycerine induction and onset of acute kidney injury and ischemia resulted in statistically significant improvement in comparison to the vehicle group in the mean tubulointerstitial score (1.15±0.08 vs. 2.00±0.00 for Group 3 vs. Group 2, respectively, p<0.01), and mean total histopathological score (2.15±0.08 vs. 3.20±0.14 for Group 3 vs. Group 2, respectively, p<0.01). These results indicate a beneficial effect in administering Compound I to prevent or reducing acute kidney damage (e.g. tubular epithelial cell necrosis, tubulointerstitial necrosis) such as caused or induced by rhabdomyolysis.

Example 4—Cisplatin-Induced Acute Kidney Injury Model in Mice

The efficacy of Compound I against cisplatin-induced acute kidney injury (AKI) is tested in a mouse model. On Day 1 of the 4-day (72 h) study, 5 mg/kg of cisplatin is administered intraperitoneally to the all of the groups defined in Table 5 below, with the exception of the control group (Group I). One hour before the cisplatin is administered, i.v. 0.9% saline water is administered to the model group (Group 2). Compound I is administered to Groups 3 and 4, and cyclosporin A (CsA) is administered to Group 5. The respective treatments are administered to the test groups on Day 2 and Day 3 of the study, 24 h and 48 h respectively from initiation of the model (t=0 with injection of cisplatin).

TABLE 5

| Group No. | Treatment | Number of rats | Volume mL/kg | Dose mg/kg | Administration | Frequency |
|---|---|---|---|---|---|---|
| 1 | Control | 8 | — | — | — | — |
| 2 | Model[a] | 8 | 5 | — | i.v.[b] | 3 times in total |
| 3 | Compound I | 8 | 5 | 3 | i.v.[b] | 3 times in total |
| 4 | Compound I | 8 | 5 | 6 | i.v.[b] | 3 times in total |
| 5 | CsA | 8 | 5 | 6 | i.v.[b] | 3 times in total |

[a]0.9% saline water.
[b]i.v from tail vein ≥ 3min.

Physiological assay and histopathology analysis of kidney tissues in analogy to those as described in the Examples above is performed on the study group animals at baseline and at defined intervals/at the end of the study (72 h after cisplatin injection). It is expected that Compound I will demonstrate an effect with respect to the treatment and/or protection against cisplatin-induced acute kidney injury.

Example 5—Formulation of Compound I

An injectable formulation of Compound I was prepared according to the following protocol:

(1) Lyophilized Powder (100 mg Compound I Per Vial)

| Composition | Amount (mg) |
|---|---|
| Compound I | 100.00 |
| Acetic acid | 12.50 |
| Water for injection | 1237.50 |

Acetic acid and water for injection was weighed and combined to prepare a 1% acetic acid solution. Compound I was added and stirred until the solution became clear. The pH of this composition is between ca. 4.0-4.3. After sterilization by filtration, filling, lyophilization and capping, the lyophilized powder comprising Compound I was obtained.

(2) Reconstitution Solvent (5 g Per Vial)

| Composition | Amount (mg) |
|---|---|
| Acetic acid | 50.00 |
| Anhydrous sodium acetate | 21.00 |
| Tween 80 (for injection) | 100.00 |
| Water for injection | 4829.00 |

Water for injection, anhydrous sodium acetate, acetic acid and Tween 80 were combined and stirred until all components were dissolved. The reconstitution solvent (pH 3.7 to 4.4) is obtained after sterilization by filtration, filling and capping.

To prepare a composition for intravenous injection, the lyophilized powder was solved in the reconstitution solvent to provide a clear solution. The solution may then be further diluted with saline water (e.g. 0.9% saline water), or glucose water (e.g. 5% glucose water) to desired concentration of Compound I for i.v. administration. It is observed, that these formulations of Compound I are clear, i.e. stable solutions (at least up to 18 h prior to use), in which Compound I remains fully dissolved i.e. not in the form of a micellar solution or in any phase-separated form.

Example 6—Formulation of Compound I for Bolus Injection

A formulation of Compound I which is suitable for bolus injection was prepared according to the following protocol:

| Composition | Amount (mg) |
|---|---|
| Compound I | 150 |
| Succinic acid | 17.7 |
| Tween 80 | 60 |
| NaOH | for pH adjustment to 5.4-5.6 |
| Water | 3000 |

0.295 g succinic acid was dissolved in water to provide a 50-ml solution. To 5 ml of the succinic acid solution, 100 mg Tween 80 was added to make a solution. 3 mL of this aq. succinic acid/Tween 80 solution was added to 150 mg of Compound I in a 10-ml vial, and sonicated until Compound I was dissolved. 1M NaOH water solution was added to adjust pH to 5.4-5.6. The mixture was further sonicated to form a solution, and then filtered using a 0.22 µm filter to provide a filtrate which is a clear solution suitable for bolus injection.

Example 7—Formulation of Compound I for Bolus Injection

A formulation of Compound I which is suitable for bolus injection was prepared according to the following protocol:

| Composition | Amount (mg) |
|---|---|
| Compound I | 150 |
| Succinic acid | 17.7 |
| PEG400 | 300 |
| NaOH | For PH adjustment to 5.4-5.6 |
| Water | 3000 |

Water was added to 0.295 g succinic acid and 5.0 g PEG 400 to provide a 50 ml solution. 3 ml of this solution was added to 150 mg of Compound I in a 10-ml vial. The resulting mixture was sonicated to provide a solution. 1M NaOH water solution was added to adjust pH to 5.4-5.6, and further sonicated. The resulting solution was filtered with a 0.22 µm filter to provide a filtrate in the form of a clear solution suitable for bolus injection.

The invention claimed is:

1. A method for the prevention and/or treatment of a kidney condition or disease in a subject exposed to a nephrotoxin capable of inducing said kidney condition or disease, wherein the nephrotoxin is a nephrotoxic drug substance, and wherein the method comprises administering to said subject Compound I, or a pharmaceutically acceptable salt thereof Compound I

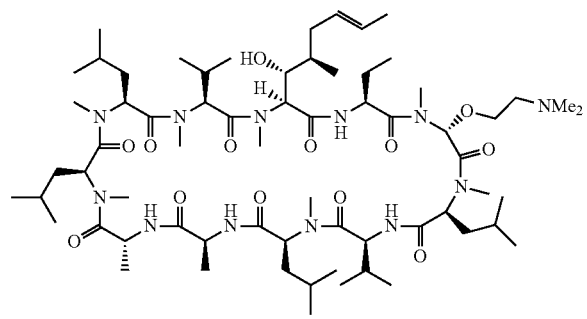

wherein the nephrotoxic drug substance is selected from the group consisting of antimicrobial agents, cancer chemotherapeutic agents, blood pressure medicines, ACE inhibitors, angiotensin receptor blockers, macrolactone immunosuppressive agents, HIV protease inhibitors, peptic ulcer medicines, non-steroidal anti-inflammatory drugs, proton pump inhibitors, laxatives and contrast agents.

2. The method according to claim 1, wherein the cancer chemotherapeutic agent is selected from the group consisting of platins, anthracyclines, bleomycins, mitomycins, actinomycins, cyclophosphamides, cytarabine, capecitabine, gemcitabine, ifosfamide, interleukin-2, streptozocin, gemtuzumab ozogamicin, melphalan, methotrexate, pemetrexed, plicamycin, and trimetrexate.

3. The method according to claim 2, wherein the subject is undergoing cancer treatment, wherein said cancer treatment comprises the administration of the chemotherapeutic agent to the subject.

4. The method according to claim 1, wherein the antimicrobial agent is selected from the group consisting of aminoglycosides, beta-lactams, polypeptide antibiotics, glycopeptide antibiotics, outer membrane protein targeting antibiotics, antifungal agent and combinations thereof.

5. The method according to claim 4, wherein the antimicrobial agent is gentamicin.

6. The method according to claim 4, wherein the subject is suffering from an infection, and wherein said infection is treated by administering the antimicrobial agent to the subject.

7. The method according to claim 1, wherein the nephrotoxic drug substance is administered to the subject repeatedly or at least twice.

8. The method according to claim 1, wherein the kidney condition or disease is nephrotoxin-induced acute kidney injury or kidney failure.

9. The method according to claim 1, wherein the kidney condition or disease is selected from rhabdomyolysis, hemolysis, myoglobinuria, and tumour lysis or myeloma-induced acute kidney injury.

10. The method according to claim 1, wherein the subject has a pre-existing condition or disease that increases the subject's risk of developing a kidney condition or disease when exposed to the nephrotoxin.

11. The method according to claim 10, wherein the subject has reduced renal function.

12. The method according to claim 1, wherein Compound I or a pharmaceutically acceptable salt thereof is administered to the subject prior to the subject's exposure to the nephrotoxic drug substance.

13. The method according to claim 1, wherein a dose of Compound I or a pharmaceutically acceptable salt thereof is administered to the subject 24 hours or less, 6 hours or less, or 2 hours or less, before a dose of the nephrotoxic drug substance is administered to the subject.

14. The method according to claim 1, wherein Compound I or a pharmaceutically acceptable salt thereof is administered repeatedly to a subject during a first period of time which commences before and overlaps with a second period of time wherein the subject is exposed repeatedly to the nephrotoxic drug substance.

15. The method according to claim 1, wherein Compound I or a pharmaceutically acceptable salt thereof is administered to the subject at a dose of about 0.001 to 10 mg/kg.

16. The method according to claim 1, wherein the subject is a human subject.

17. The method according to claim 1, wherein Compound I or a pharmaceutically acceptable salt thereof is formulated for administration by infusion or by injection.

18. A method for the prevention and/or reduction of blood urea nitrogen levels of at least 1.5 to 3 times higher than baseline and/or serum creatinine levels of at least 1.5 to 3 times higher than baseline in a subject exposed to a nephrotoxin, wherein the nephrotoxin is a nephrotoxic drug substance, the method comprising administering to said subject Compound I or a pharmaceutically acceptable salt thereof

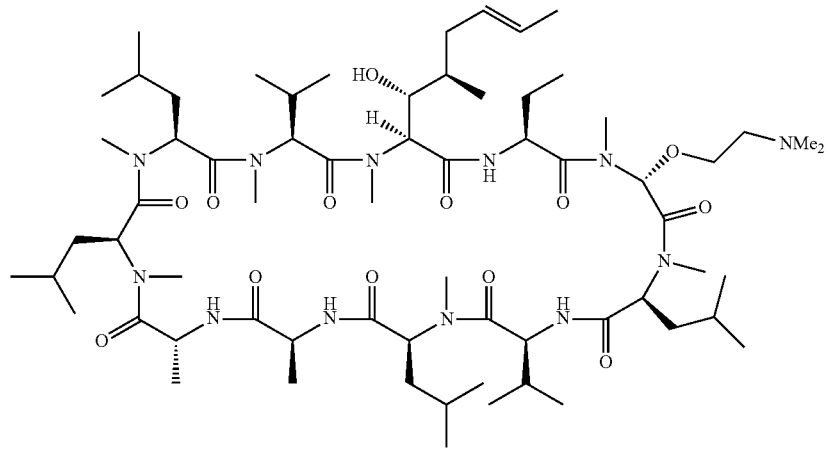

Compound I wherein the nephrotoxic drug substance is selected from the group consisting of antimicrobial agents, cancer chemotherapeutic agents, blood pressure medicines, ACE inhibitors, angiotensin receptor blockers, macrolactone immunosuppressive agents, HIV protease inhibitors, peptic ulcer medicines, non-steroidal anti-inflammatory drugs, proton pump inhibitors, laxatives and contrast agents.

19. The method according to claim 7, wherein the nephrotoxic drug substance is administered once daily over a period of at least 3 days, or at least 7 days.

20. The method according to claim 10, wherein said pre-existing kidney condition is chronic kidney disease, or wherein the subject has a history of renal impairment or requires dialysis.

21. The method according to claim 11, wherein the subject has blood urea nitrogen levels of at least 1.5 to 3 times higher than baseline, and/or serum creatinine levels at least 1.5 to 3 times higher than baseline, and/or oliguria.

22. The method according to claim 15, wherein the dose is about 0.1 to 10 mg/kg.

* * * * *